(12) United States Patent
Kim et al.

(10) Patent No.: US 11,793,050 B2
(45) Date of Patent: Oct. 17, 2023

(54) DISPLAY DEVICE WITH CALCULATION OF BODY COMPOSITION BASED ON SIGNAL THROUGH INPUT SENSOR

(71) Applicant: SAMSUNG DISPLAY CO., LTD., Yongin-si (KR)

(72) Inventors: Yuna Kim, Seoul (KR); Soojung Lee, Suwon-si (KR); Seungwook Chun, Daegu (KR); Boram Choi, Asan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 17/365,938

(22) Filed: Jul. 1, 2021

(65) Prior Publication Data

US 2022/0115450 A1 Apr. 14, 2022

(30) Foreign Application Priority Data

Oct. 8, 2020 (KR) .......................... 10-2020-0130499

(51) Int. Cl.
*G06F 3/041* (2006.01)
*H10K 59/40* (2023.01)
(Continued)

(52) U.S. Cl.
CPC ............. *H10K 59/40* (2023.02); *A61B 5/443* (2013.01); *G06F 3/011* (2013.01); *G06F 3/0412* (2013.01); *G06F 3/0416* (2013.01); *G06F 3/0446* (2019.05); *G06F 3/0448* (2019.05); *A61B 2562/0214* (2013.01); *G06F 2203/04112* (2013.01)

(58) Field of Classification Search
CPC ...... G06F 3/011; G06F 3/0412; G06F 3/0416; G06F 3/0446; G06F 3/04166
See application file for complete search history.

(56) References Cited

U.S. PATENT DOCUMENTS 8,884,917 B2 11/2014 Seo
11,171,185 B2 * 11/2021 Kim ...................... A61B 5/443
(Continued)

FOREIGN PATENT DOCUMENTS

KR          10-0634544      10/2006
KR      10-2016-0101580      8/2016
(Continued)

OTHER PUBLICATIONS

Oberg et al.,27th Edition Machinery's Hanbook, 2004, Industrial Press Inc, p. 40 (Year: 2004).*

*Primary Examiner* — Liliana Cerullo
(74) *Attorney, Agent, or Firm* — H.C. Park & Associates, PLC

(57) ABSTRACT

A display device includes a display panel that displays an image, an input sensor arranged on the display panel and including transmission electrodes and reception electrodes electrically insulated from the transmission electrodes, and a readout circuit connected to the input sensor, wherein the readout circuit sequentially outputs a transmission signal to a portion of the transmission electrodes corresponding to a body composition sensing region and receives a reception signal from a portion of the reception electrodes corresponding to the body composition sensing region.

6 Claims, 19 Drawing Sheets

(51) Int. Cl.
*G06F 3/044* (2006.01)
*A61B 5/00* (2006.01)
*G06F 3/01* (2006.01)

(56) References Cited

U.S. PATENT DOCUMENTS

| | | |
|---|---|---|
| 2006/0281981 A1 | 12/2006 | Jang et al. |
| 2014/0018641 A1* | 1/2014 | Yoshino ............... A61B 5/7275 |
| | | 600/301 |
| 2016/0239148 A1 | 8/2016 | Lee et al. |
| 2016/0274726 A1* | 9/2016 | Chung .................... G06F 3/014 |
| 2017/0336909 A1* | 11/2017 | Song ................... G06F 3/04166 |
| 2018/0190723 A1* | 7/2018 | Han ...................... G06F 3/0446 |
| 2019/0056823 A1* | 2/2019 | Stevenson ............. G06F 3/0443 |
| 2019/0187845 A1* | 6/2019 | Ye ......................... G06F 3/0412 |
| 2020/0375545 A1 | 12/2020 | Kim et al. |
| 2021/0043693 A1 | 2/2021 | Kim et al. |

FOREIGN PATENT DOCUMENTS

| | | |
|---|---|---|
| KR | 10-1715858 | 3/2017 |
| KR | 10-1747731 | 6/2017 |
| KR | 10-2050435 | 11/2019 |
| KR | 10-2020-0139296 | 12/2020 |

\* cited by examiner

DISPLAY DEVICE WITH CALCULATION OF BODY COMPOSITION BASED ON SIGNAL THROUGH INPUT SENSOR

CROSS-REFERENCE TO RELATED APPLICATIONS

This application claims priority from and the benefit of Korean Patent Application No. 10-2020-0130499, filed on Oct. 8, 2020, which is hereby incorporated by reference for all purposes as if fully set forth herein.

BACKGROUND

Field

The disclosure relates to a display device. Multimedia electronic devices such as televisions, mobile phones, tablets, computers, navigation devices, game machines, and the like are provided with a display device for displaying an image. Electronic devices may be provided with not only typical input units such as buttons, keyboards, mice, and the like, but also a display device capable of providing touch based input schemes for enabling users to intuitively and conveniently input information or commands with ease.

Discussion of the Background

Multimedia electronic devices such as televisions, mobile phones, tablets, computers, navigation devices, game machines, and the like are provided with a display device for displaying an image. Electronic devices may be provided with not only typical input units such as buttons, keyboards, mice, and the like, but also a display device capable of providing touch-based input schemes for enabling users to intuitively and conveniently input information or commands with ease. With the increasing use of personal electronic devices such as mobile phones, the necessity of display devices capable of sensing and displaying biometric information increases.

The above information disclosed in this Background section is only for understanding of the background of the inventive concepts, and, therefore, it may contain information that does not constitute prior art.

1. SUMMARY

The present disclosure provides a display device capable of sensing biometric information about a user.

Additional features of the inventive concepts will be set forth in the description which follows, and in part will be apparent from the description, or may be learned by practice of the inventive concepts.

An embodiment of the inventive concepts provides a display device including a display panel that displays an image, an input sensor arranged on the display panel and including transmission electrodes and reception electrodes electrically insulated from the transmission electrodes, and a readout circuit connected to the input sensor, wherein the readout circuit sequentially outputs a transmission signal to a portion of the transmission electrodes corresponding to a body composition sensing region, and receives a reception signal from a portion of the reception electrodes corresponding to the body composition sensing region.

The input sensor may include transmission lines respectively connected to the transmission electrodes between the readout circuit and the transmission electrodes, and reception lines respectively connected to the reception electrodes between the readout circuit and the reception electrodes.

Transmission lines that are disposed outside the body composition sensing region among the transmission lines and reception lines that are disposed outside the body composition sensing region among the reception lines may be in a floating state.

The readout circuit may include a transmitter that is configured to output the transmission signal, which is in the active level, to the transmission lines, a receiver that is configured to receive the reception signal from the reception lines, and a control circuit that is configure to control the transmitter and the receiver.

The control circuit may include an analog-to-digital converter that is configured to convert the reception signal into a digital reception signal, and a body composition calculator that is configured to calculate a body composition of a user based on the digital reception signal.

During a normal mode, the readout circuit may sequentially output the transmission signal, which is in the active level, to all of the transmission electrodes, and may receive the reception signal from all of the reception electrodes.

During a body composition sensing mode, the readout circuit may sequentially output the transmission signal, which is in the active level, to the portion of the transmission electrodes corresponding to the body composition sensing region, and may receive the reception signal from the portion of the reception electrodes corresponding to the body composition sensing region.

The body composition sensing region may correspond to at least one and less than x in number of transmission electrodes (where x is a positive integer value) among x in number of transmission electrodes and correspond to at least one and less than y in number of reception electrodes (where y is a positive integer value) among y in number of reception electrodes.

The readout circuit may output a transmission signal, which is in a ground voltage level, to another portion of the transmission electrodes not corresponding to the body composition sensing region, and may maintain, at the ground voltage level, a reception signal received from another portion of the reception electrodes not corresponding to the body composition sensing region.

The readout circuit may sequentially output the transmission signal, which is in the active level, to the transmission electrodes, and may receive the reception signal from the reception electrodes, wherein the body composition sensing region may correspond to any one transmission electrode that receives the transmission signal, which is in the active level, among the transmission electrodes and any one reception electrode among the reception electrodes.

The readout circuit may include an analog-to-digital converter that is configured to convert the reception signal into a digital reception signal, and a body composition calculator that is configured to calculate a body composition of a user based on the digital reception signal.

The body composition calculator may calculate a moisture level y using equation y=a+(b×DSX) where each of 'a' and 'b' is a preset constant, and DSX denotes the digital reception signal.

Each of the transmission electrodes and the reception electrodes may have a mesh shape.

In an embodiment of the inventive concepts, a display device includes a display panel that displays an image, an input sensor arranged on the display panel and including transmission electrodes and reception electrodes electrically insulated from the transmission electrodes, and a readout circuit connected to the input sensor, wherein the readout circuit sequentially outputs a transmission signal to the transmission electrodes. and sequentially receives a reception signal from the reception electrodes.

The readout circuit may include a transmitter that is configured to output the transmission signal, which is in the active level, to transmission lines, a receiver that is configured to receive the reception signal from reception lines, and a control circuit that is configured to control the transmitter and the receiver.

The control circuit may include an analog-to-digital converter that is configured to convert the reception signal into a digital reception signal, and a body composition calculator that is configured to calculate a body composition of a user based on the digital reception signal.

The body composition calculator may calculate a moisture level y using equation $y=a+(b \times DSX)$ where each of 'a' and 'b' is a preset constant, and DSX denotes the digital reception signal.

The reception signal may indicate a capacitance variation in a body composition sensing region, in which a transmission electrode that receives the transmission signal, which is in the active level, among the transmission electrodes and any one of the reception electrodes intersect.

The input sensor may include transmission lines respectively connected to the transmission electrodes and that is provided between the readout circuit and the transmission electrodes, and reception lines respectively connected to the reception electrodes and that is provided between the readout circuit and the reception electrodes.

Transmission lines that are disposed outside the body composition sensing region among the transmission lines, and reception lines that are disposed outside the body composition sensing region among the reception lines may be in a floating state.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

Figure 1:
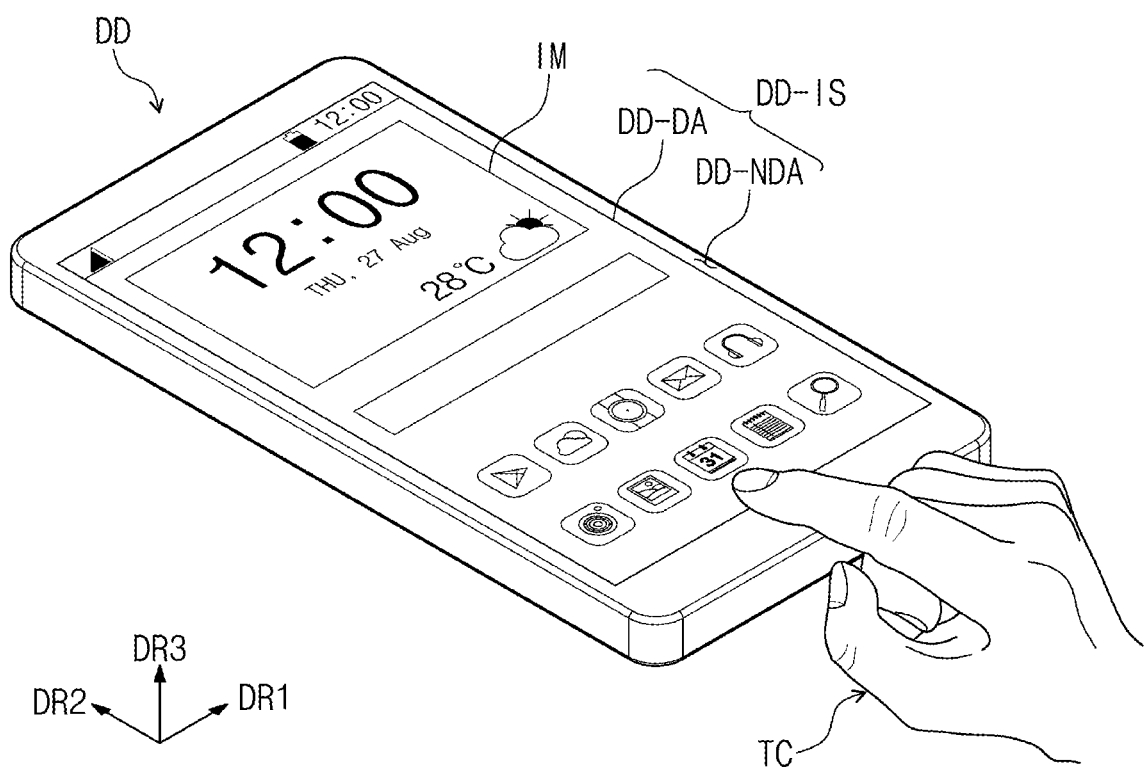
FIG. 1 is a perspective view illustrating a display device according to an embodiment of the inventive concepts.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element or layer is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the DR1-axis, the DR2-axis, and the DR3-axis are not limited to three axes of a rectangular coordinate system, such as the x, y, and z-axes, and may be interpreted in a broader sense. For example, the DR1-axis, the DR2-axis, and the DR3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein should be interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various embodiments are described herein with reference to sectional and/or exploded illustrations that are schematic illustrations of idealized embodiments and/or intermediate structures. As such, variations from the shapes of the illustrations as a result, for example, of manufacturing techniques and/or tolerances, are to be expected. Thus, embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some embodiments may be physically separated into two or more interacting and discrete blocks, units, and/or modules without departing from the scope of the inventive concepts. Further, the blocks, units, and/or modules of some embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

FIG. 1 is a perspective view illustrating a display device DD according to an embodiment that is constructed according to principles of the invention.

As illustrated in FIG. 1, the display device DD may display an image IM through a display surface DD-IS. The display surface DD-IS is parallel to a plane defined by a first direction axis DR1 and a second direction axis DR2 that is orthogonal to the first direction axis DR1. A normal direction of the display surface DD-IS, i.e., a thickness direction of the display device DD, is indicated by a third direction axis DR3 that is orthogonal to both the first direction axis DR1 and the second direction axis DR2 (i.e., DR1, DR2, DR3 respectively correspond to x, y and z axes of an x-y-z three axis coordinate system).

Front surfaces (or top surfaces) and rear surfaces (or bottom surfaces) of each component or member described below are divided by the third direction axis DR3. However, in the embodiment as described herein, the first to third direction axes DR1 to DR3 are merely examples. Hereinafter, first to third directions are defined as directions indicated by the first to third direction axes DR1 to DR3 respectively, and referred to by the same reference signs.

In an embodiment as descried herein, the display device DD is illustrated as having a flat display surface, but embodiments of the inventive concepts are not limited thereto. The display device DD may further include a curved display surface. The display device DD may include a three-dimensional display surface. The three-dimensional display surface may include a plurality of display regions indicating different directions, and may include, for example, a polygonal column-type display surface.

The display device DD according to the embodiment described herein may be a rigid display device. However, display devices DD according to embodiments of the inventive concepts are not limited thereto, and may be a flexible display device. The flexible display device may include a foldable display device, a bending-type display device which is partially bent, or a slidable display device.

In the embodiment, the display device DD that is applicable to a mobile phone is illustrated in FIG. 1. Although not illustrated, electronic modules, a camera module, a power supply module, etc., mounted on a main board, may be arranged in a bracket/case or the like together with the display device DD to constitute a mobile phone. The display device DD according to an embodiment may be applied to a large-size electronic device such as a television, a monitor, or the like, or a small- or medium-size electronic device such as a tablet, a vehicle navigation device, a game machine, a smart watch, or the like.

As illustrated in FIG. 1, the display surface DD-IS includes an image region DD-DA in which the image IM is displayed and a bezel region DD-NDA adjacent to the image region DD-DA. An image is not displayed in the bezel region DD-NDA. FIG. 1 illustrates time and icon images as an example of the image IM.

As illustrated in FIG. 1, the image region DD-DA may have a substantially rectangular shape. The term "substantially rectangular shape" includes not only a mathematical rectangle shape but also a rectangle shape in which curved boundaries rather than vertices are defined in vertex regions (or corner regions).

The bezel region DD-NDA may surround the image region DD-DA. However, embodiments of the inventive concepts are not limited thereto, and the image region DD-DA and the bezel region DD-NDA may be designed to have different shapes. The bezel region DD-NDA may be arranged on only one side of the image region DD-DA. The bezel region DD-NDA may not be exposed to the outside according to a combination form of other components of an electronic device and the display device DD.

The display device DD according to an embodiment may sense a user input TC applied externally. The display device DD may sense the user input TC by detecting a change in any one of or combination of reflected light, temperature, pressure, ultrasonic waves, and electromagnetism caused by the user input TC. In the embodiment described herein, the user input TC is assumed to be a touch input applied from a user's hand to a front surface of the display device DD, but this is merely illustrative, and the user input TC may be provided in various forms as described above. Furthermore, the display device DD may sense the user input TC applied to a side or rear surface of the display device DD according to a structure of the display device DD, but is not limited to a certain embodiment.

Furthermore, the display device DD according to an embodiment may sense an input from an electronic pen. The electronic pen may be an input device using a mechanism such as a stylus pen, an electronic pen, or an active pen.

Figure 2:
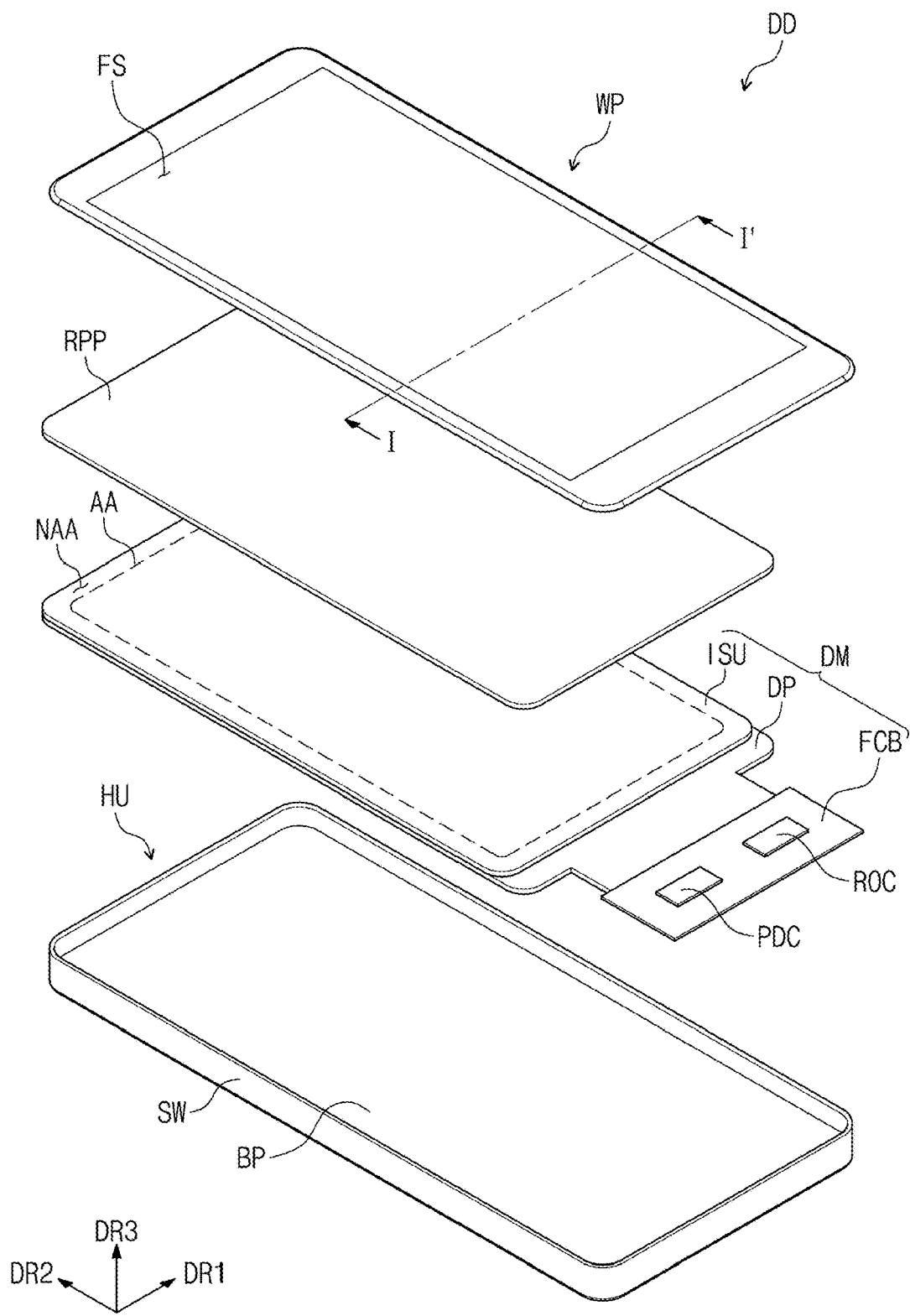
FIG. 2 is an exploded perspective view of a display device according to an embodiment of the inventive concepts.

FIG. 2 is an exploded perspective view of a display device according to an embodiment.

Referring to FIG. 2, the display device DD may include a window WP, an anti-reflective panel RPP, a display module DM, and a housing HU. As illustrated in FIGS. 1 and 2, in the present embodiment, the window WP and the housing HU are coupled to each other to form an exterior of the display device DD.

The window WP protects an upper surface of the display panel DP. The window WP may include an optically clear insulating material. For example, the window WP may include a front surface FS including glass or plastic. The window WP may have a multi-layer structure or single-layer structure. For example, the window WP may include a plurality of plastic films bonded by an adhesive or may include a glass substrate and a plastic film bonded by an adhesive.

The anti-reflective panel RPP may be arranged under the window WP. The anti-reflective panel RPP reduces a reflection ratio of external light incident from above the window WP. In an embodiment, the anti-reflective panel RPP may not be provided or may be embedded in the display module DM.

The display module DM may display the image IM and sense an external input. The display module DM may include a display panel DP, an input sensor ISU, and a printed circuit board FCB.

An active region AA and a peripheral region NAA corresponding to the image region DD-DA and the bezel region DD-NDA illustrated in FIG. 1 may be defined in the display panel DP. The display panel DP may substantially generate the image IM. The image IM generated in the active region AA of the display panel DP is externally viewed by the user through the window WP.

The input sensor ISU senses an external input that is externally applied. As described above, the input sensor ISU may sense an external input provided to the window WP.

The display panel DP may be electrically connected to the printed circuit board FCB. In an embodiment, a driving chip, which generates signals required for operating the display panel DP, may be mounted in the display panel DP.

The printed circuit board FCB may include various driving circuits for driving the display panel DP and the input sensor ISU or a connector for supplying power. In an embodiment, the printed circuit board FCB may include a panel driving circuit PDC for driving the display panel DP and a readout circuit ROC for driving the input sensor ISU. Each of the panel driving circuit PDC and the readout circuit ROC may be formed as an integrated circuit and mounted on the printed circuit board FCB. In another embodiment, the panel driving circuit PDC and the readout circuit ROC may be configured as one integrated circuit.

The housing HU includes a bottom portion BP and a sidewall SW. The sidewall SW may extend from the bottom portion BP. The housing HU may accommodate the display panel DP in an accommodation space defined by the bottom portion BP and the sidewall SW. The window WP may be coupled to the sidewall SW of the housing HU. The sidewall SW of the housing HU may support an edge of the window WP.

The housing HU may include a material having a relatively high rigidity. For example, the housing HU may include glass, plastic, or metal, or may include a plurality of frames and/or plates configured with a combination thereof. The housing HU may stably protect components of the display device DD accommodated in the internal space from an external impact.

Figure 3:
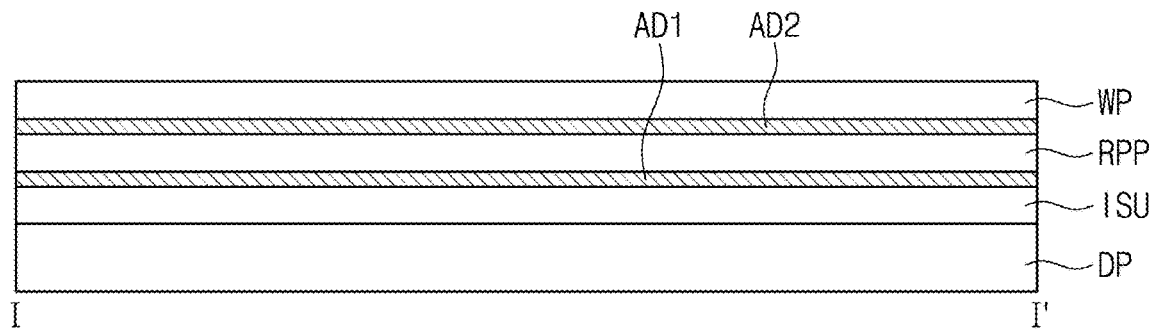
FIG. 3 is a diagram illustrating a cross-section taken along line I-I' of FIG. 2.
Figure 3:
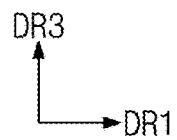

FIG. 3 is a diagram illustrating a cross-section taken along line I-I' of FIG. 2.

FIG. 3 illustrates a cross-section of the display device DD defined by the first direction axis DR1 and the third direction axis DR3. FIG. 3 simply illustrates the components of the display device DD to describe a positional relationship between the components.

The display device DD according to an embodiment may include the display panel DP, the input sensor ISU, the anti-reflective panel RPP, and the window WP. At least some of the display panel DP, the input sensor ISU, the anti-reflective panel RPP, and the window WP may be formed through a continuous process or may be coupled to each other using an adhesive member. For example, the input sensor ISU and the anti-reflective panel RPP may be coupled by an adhesive member AD1. The anti-reflective panel RPP and the window WP may be coupled by an adhesive member AD2.

The adhesive members AD1 and AD2 may be a transparent adhesive member such as a pressure sensitive adhesive (PSA) film, an optically clear adhesive (OCA) film, or an optically clear resin (OCR). The adhesive members described below may include a typical adhesive or removable adhesive. In an embodiment, the anti-reflective panel RPP and the window WP may be replaced with other components or may not be provided.

In FIG. 3, among the input sensor ISU, the anti-reflective panel RPP, and the window WP, the input sensor ISU which is formed with the display panel DP through a continuous process is directly arranged on the display panel DP. In the present disclosure, the wording "B is directly arranged on A" represents that an additional adhesive layer/adhesive member is not arranged between A and B. Component B is formed through a continuous process on a base surface provided by component A after component A is formed.

In the embodiment described herein, the anti-reflective panel RPP and the window WP are a type of "panel", and the input sensor ISU is a type of "layer". The "panel" type includes a base layer that provides a base surface, for example, a synthetic resin film, a composite material film, a glass substrate, or the like, but the "layer" type may not provide the base layer. In other words, "layer"-type components are arranged on the base surface provided by another component. In an embodiment, the anti-reflective panel RPP and the window WP may be a type of "layer".

The display panel DP generates an image, and the input sensor ISU obtains coordinate information about an external input (e.g., a touch event). The display device DD according to an embodiment may further include a protective member arranged on a lower surface (or rear surface) of the display panel DP. The protective member and the display panel DP may be coupled to each other through an adhesive member.

The display panel DP according to an embodiment may be an emissive display panel, but is not particularly limited. For example, the display panel DP may be an organic light-emitting display panel or a quantum dot light-emitting display panel. The above panels are differentiated according to a material of a light-emitting element. For example, an emission layer of an organic light-emitting display panel may include an organic light-emitting material. An emission layer of a quantum dot light-emitting display panel may include quantum dots and/or quantum rods, etc. Hereinafter, the display panel DP will be described as an organic light-emitting display panel.

The anti-reflective panel RPP reduces a reflection ratio of external light incident from above the window WP. The anti-reflective panel RPP according to an embodiment may include a phase retarder and a polarizer. The phase retarder may be a type of a film or a type of a liquid crystal coating. The polarizer may also be a type of a film or a type of a liquid crystal coating. The film type may include a stretched synthetic resin film, and the liquid crystal coating type may include liquid crystals arranged in a predetermined array. The phase retarder and the polarizer may further include a protective film. The phase retarder and polarizer itself or the protective film thereof may be defined as the base layer of the anti-reflective panel RPP.

The anti-reflective panel RPP according to an embodiment may include color filters. The color filters have a predetermined array. The array of the color filters may be determined in consideration of emitted light colors of pixels included in the display panel DP. The anti-reflective panel RPP may further include a black matrix adjacent to the color filters.

The anti-reflective panel RPP according to an embodiment may include a destructive interference structure. For example, the destructive interference structure may include a first reflective layer and a second reflective layer arranged on different layers. First reflected light and second reflected light respectively reflected from the first reflective layer and the second reflective layer may destructively interfere with each other, thereby reducing the reflection ratio of external light.

The window WP according to an embodiment may include a glass substrate and/or a synthetic resin film. The window WP is not limited to a single layer. The window WP may include two or more films coupled by an adhesive member. Although not illustrated, the window WP may further include a functional coating layer. The functional coating layer may include an anti-fingerprint layer, an anti-reflective layer, a hard coating layer, etc.

The input sensor ISU and the display panel DP are described in detail below.

Figure 4:
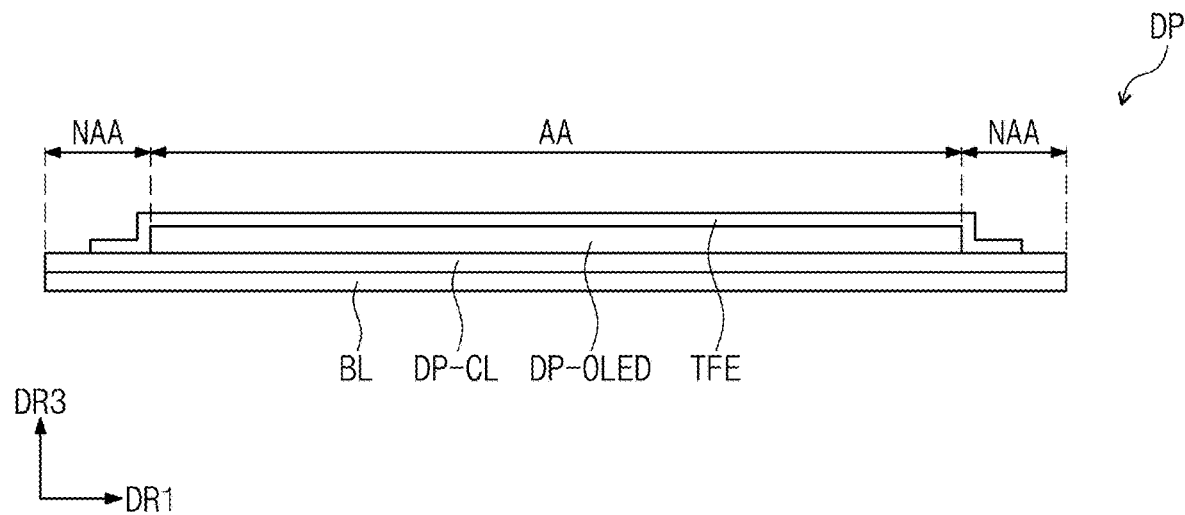
FIG. 4 is a cross-sectional view of the display panel illustrated in FIG. 3.
Figure 4:
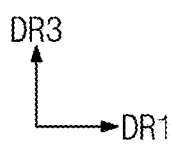

FIG. 4 is a cross-sectional view of the display panel DP illustrated in FIG. 3.

As illustrated in FIG. 4, the display panel DP includes a base layer BL, and a circuit element layer DP-CL, a light-emitting element layer DP-OLED, and a thin-film encapsulation layer TFE, arranged on the base layer BL. The active region AA and the peripheral region NAA corresponding to the image region DD-DA and the bezel region DD-NDA illustrated in FIG. 1 may be defined in the display panel DP. In the embodiments described herein, the wording "region/portion corresponds to another region/portion" represents "overlapping each other", but is not limited to cases in which the regions/portions have the same area and/or the same shape.

The base layer BL may include at least one synthetic resin film. The base layer BL may include a glass substrate, a metal substrate, an organic/inorganic composite material substrate, or the like.

The circuit element layer DP-CL is arranged on the base layer BL. The circuit element layer DP-CL includes at least one insulating layer and circuit elements. The insulating layer includes at least one inorganic layer and at least one organic layer. The circuit elements may include signal lines, a pixel driving circuit, and the like.

The light-emitting element layer DP-OLED is arranged on the circuit element layer DP-CL. The light-emitting element layer DP-OLED may include organic light-emitting diodes. The light-emitting element layer DP-OLED may further include an organic layer such as a pixel defining film.

The thin-film encapsulation layer TFE may be arranged on the light-emitting element layer DP-OLED so as to encapsulate the light-emitting element layer DP-OLED. The thin-film encapsulation layer TFE may overall cover the active region AA. The thin-film encapsulation layer TFE may cover a portion of the peripheral region NAA.

The thin-film encapsulation layer TFE includes a plurality of thin films. A portion of the thin films is disposed to improve optical efficiency, and another portion of the thin films is disposed to protect the organic light-emitting diodes.

Figure 5:
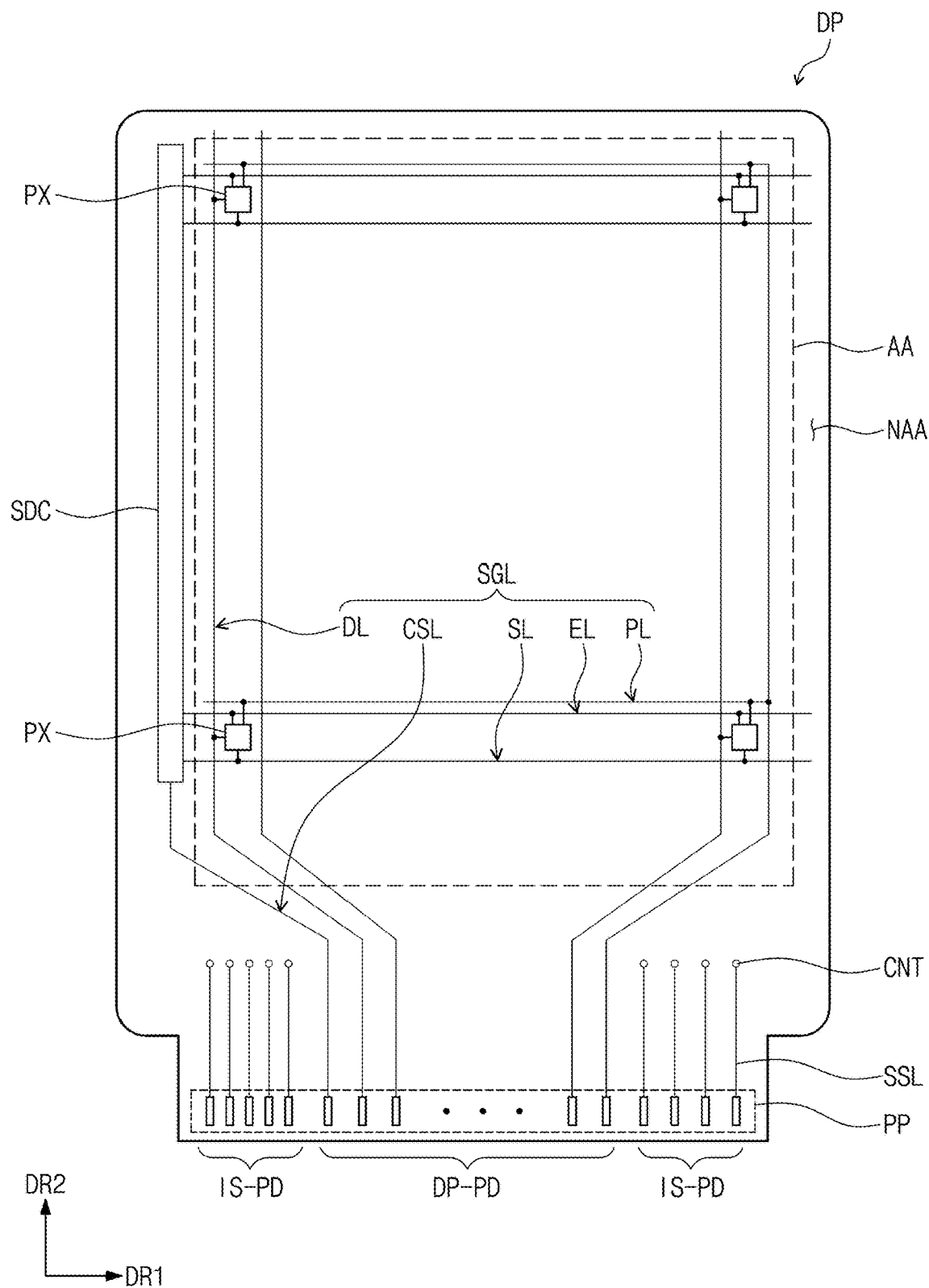
FIG. 5 is a planar view illustrating a display panel according to an embodiment of the inventive concepts.

FIG. 5 is a planar view illustrating the display panel DP according to an embodiment.

As illustrated in FIG. 5, the display panel DP may include a scan driving circuit SDC, a plurality of signal lines SGL, a plurality of signal pads DP-PD and IS-PD, and a plurality of pixels PX.

The scan driving circuit SDC generates a plurality of scan signals, and sequentially outputs the scan signals to a plurality of scan lines SL that will be described later. The scan driving circuit SDC may output not only the scan signals but also other control signals to the pixels PX.

The scan driving circuit SDC may include a plurality of transistors formed through the same process as transistors in the pixels PX.

The signal lines SGL include the scan lines SL, data lines DL, a power supply line PL, emission control lines EL, and a control signal line CSL. Each of the scan lines SL, the data lines DL, and the emission control lines EL is connected to a corresponding pixel PX among the pixels PX. The power supply line PL is commonly connected to the pixels PX. The control signal line CSL may provide control signals to the scan driving circuit SDC. The power supply line PL may provide a voltage required for operating the pixels PX. The power supply line PL may include a plurality of lines for providing different voltages.

In the embodiment described herein, the signal lines SGL may further include auxiliary lines SSL. In an alternative implementation of the embodiment, the auxiliary lines SSL may not be provided. The auxiliary lines SSL are respectively connected to contact holes CNT. The auxiliary lines SSL may be electrically connected via the contact holes CNT to signal lines of the input sensor ISU (refer to FIG. 6) that will be described later.

The display panel DP may include a pad region PP. The plurality of signal pads DP-PD and IS-PD may be arranged in the pad region PP of the display panel DP. The signal pads DP-PD and IS-PD may include first-type signal pads DP-PD connected to the data lines DL, the power supply line PL, and the control signal line CSL and second-type signal pads IS-PD connected to the auxiliary lines SSL. The first-type signal pads DP-PD and the second-type signal pads IS-PD are arranged adjacent to each other in the pad region PP defined in a portion of the peripheral region NAA. The signal pads DP-PD and IS-PD may have layer structures or materials which are not differentiated, and may be formed through the same process.

The active region AA may be defined as a region in which the pixels PX are arranged. A plurality of electronic elements are arranged in the active region AA. The electronic elements include an organic light-emitting diode provided to each of the pixels PX and a pixel driving circuit connected to the organic light-emitting diode. The scan driving circuit SDC, the signal lines SGL, the signal pads DP-PD and IS-PD, and the pixel driving circuit may be included in the circuit element layer DP-CL illustrated in FIG. 4.

Each of the pixels PX may include a plurality of transistors, a capacitor, and an organic light-emitting diode. The pixels PX emit light in response to signals received through the scan lines SL, the data lines DL, the emission control lines EL, and the power supply line PL.

The signal pads DP-PD and IS-PD of the display panel DP may be electrically connected to the printed circuit board FCB illustrated in FIG. 2.

The display panel DP illustrated in FIG. 5 may be partially bent. A portion of the peripheral region NAA of the display panel DP may be bent, wherein the portion may be bent with respect to a bending axis parallel to the first direction DR1. The bending axis may be defined overlapping a portion of the data lines DL and a portion of the auxiliary lines SSL.

Figure 6:
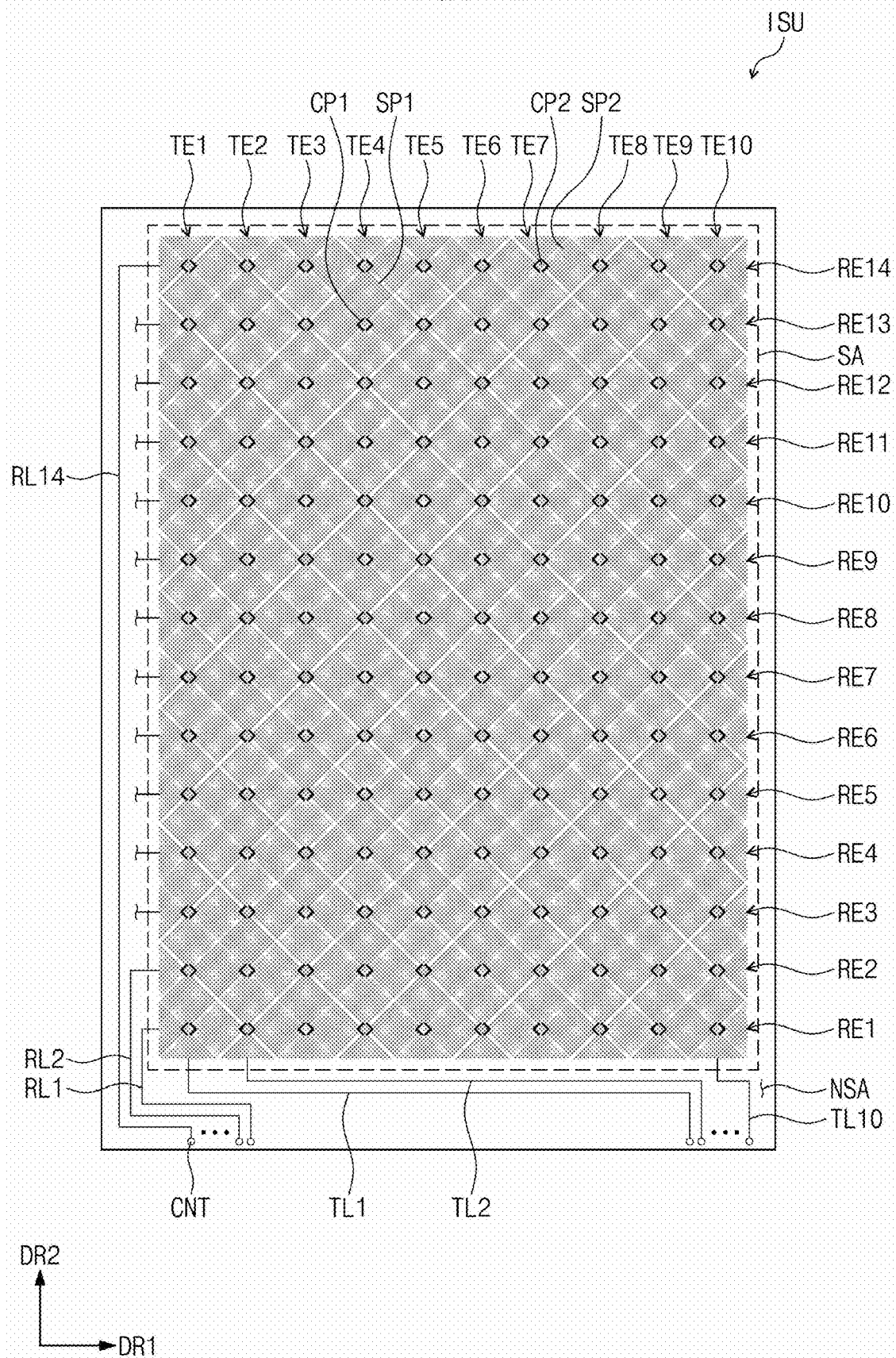
FIG. 6 is a planar view illustrating a configuration of an input sensor according to an embodiment of the inventive concepts.

FIG. 6 is a planar view illustrating a configuration of the input sensor ISU according to an embodiment.

Referring to FIG. 6, the input sensor ISU may include a sensing region SA and a non-sensing region NSA. The sensing region SA may be a region that is activated in response to an electric signal. In an embodiment, the sensing region SA may be a region in which an input is sensed. The non-sensing region NSA may surround the sensing region SA. The sensing region SA may correspond to the active region AA of FIG. 5, and the non-sensing region NSA may correspond to the peripheral region NAA of FIG. 5.

The input sensor ISU includes transmission electrodes TE1 to TE10 and reception electrodes RE1 to RE14. The transmission electrodes TE1 to TE10 and the reception electrodes RE1 to RE14 are arranged in the sensing region SA. The transmission electrodes TE1 to TE10 and the reception electrodes RE1 to RE14 are electrically insulated from each other and intersect each other. Although the input sensor ISU includes first to 10th transmission electrodes TE1 to TE10 and first to 14th reception electrodes RE1 to RE14, embodiments of the inventive concepts are not limited thereto. The number of transmission electrodes and the number of reception electrodes may be variously changed. Although the number of reception electrodes is illustrated as being larger than the number of transmission electrodes in FIG. 6, the number of transmission electrodes may be equal to or larger than the number of reception electrodes in another embodiment.

In the embodiments described herein, the electrodes TE1 to TE10 are referred to as transmission electrodes and the electrodes RE1 to RE14 are referred to as reception electrodes in order to clearly differentiate the electrodes TE1 to TE10 and the electrodes RE1 to RE14, but functions of the electrodes are not limited by the names of the electrodes in an embodiment. According to an operation mode, the transmission electrodes TE1 to TE10 may operate not only as an transmission electrode but also as a reception electrode, and the reception electrodes RE1 to RE14 may operate not only as a reception electrode but also as a transmission electrode.

Each of the first to 10th transmission electrodes TE1 to TE10 extends in the second direction DR2. The first to 10th transmission electrodes TE1 to TE10 may be arranged spaced apart from each other in the first direction DR1. The first to 10th transmission electrodes TE1 to TE10 may be electrically separated from each other. Each of the first to 10th transmission electrodes TE1 to TE10 includes first sensing patterns SP1 arranged spaced apart from each other in the first second direction DR2 and first connection patterns CP1 that electrically connect the first sensing patterns SP1. The first sensing patterns SP1 and the first connection patterns CP1 are arranged on different layers and do not have an integrated shape.

Each of the first to 14th reception electrodes RE1 to RE14 extends in the first direction DR1. The first to 14th reception electrodes RE1 to RE14 may be arranged spaced apart from each other in the second direction DR2. The first to 14th reception electrodes RE1 to RE14 may be electrically separated from each other. The first to 14th reception electrodes RE1 to RE14 and the first to 10th transmission electrodes TE1 to TE10 may intersect each other and may be electrically insulated from each other. Each of the first to 14th reception electrodes RE1 to RE14 includes second sensing patterns SP2 arranged spaced apart from each other in the first direction DR1 and second connection patterns CP2 that electrically connect the second sensing patterns SP2. The second sensing patterns SP2 and the second connection patterns CP2 may have an integrated shape.

Although the first sensing patterns SP1 and the second sensing patterns SP2 are illustrated as having a rhombus shape, embodiments of the inventive concepts are not limited thereto. The first sensing patterns SP1 and the second sensing patterns SP2 may have different polygonal shapes.

Each of the first to 10th transmission electrodes TE1 to TE10 and each of the first to 14th reception electrodes RE1 to RE14 may have a mesh shape. Since each of the first to 10th transmission electrodes TE1 to TE10 and each of the first to 14th reception electrodes RE1 to RE14 has a mesh shape, parasitic capacitance between these electrodes and the electrodes (e.g., the second electrode CE (refer to FIG. 7)) of the display panel DP (refer to FIG. 5) may be reduced as compared to such elements not having a mesh shape.

The input sensor ISU may obtain location information about an external input based on a change in mutual capacitance between the first to 10th transmission electrodes TE1 to TE10 and the first to 14th reception electrodes RE1 to RE14.

The input sensor ISU may further include first to 10th transmission lines TL1 to TL10 and first to 14th reception lines RL1 to RL14. The first to 10th transmission lines TL1 to TL10 and the first to 14th reception lines RL1 to RL14 may be arranged in the non-sensing region NSA. The first to 10th transmission lines TL1 to TL10 are electrically connected to one sides of the first to 10th transmission electrodes TE1 to TE10, and the first to 14th reception lines RL1 to RL14 are electrically connected to one sides of the first to 14th reception electrodes RE1 to RE14. However, embodiments of the inventive concepts are not limited thereto. As an example, the input sensor ISU may further include transmission lines electrically connected to other sides of the first to 10th transmission electrodes TE1 to TE10.

The input sensor ISU is electrically connected to the readout circuit ROC (refer to FIG. 2) via the first to 10th transmission lines TL1 to TL10 and the first to 14th reception lines RL1 to RL14. The readout circuit ROC may control operation of the input sensor ISU. In an embodiment, the readout circuit ROC may control the operation of the input sensor ISU in first to fourth operation modes.

In the first to fourth operation modes, the readout circuit ROC may transmit a transmission signal to the first to 10th transmission lines TL1 to TL10 and/or the first to 14th reception lines RL1 to RL14, and may receive a reception signal from the first to 10th transmission lines TL1 to TL10 and/or the first to 14th reception lines RL1 to RL14.

The operations of the readout circuit ROC and the input sensor ISU in each of the first to fourth operation modes will be described in detail later.

Figure 7:
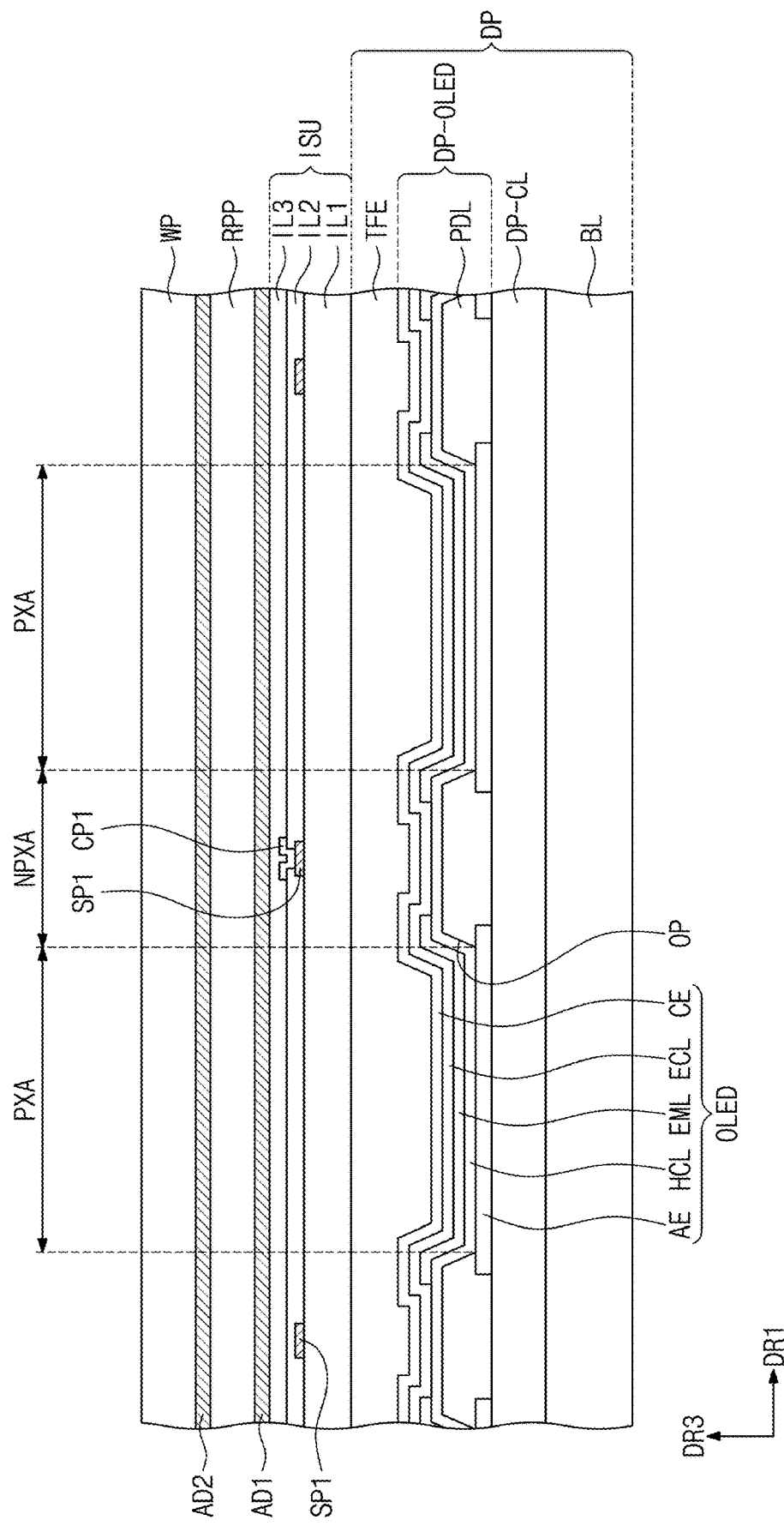
FIG. 7 is a cross-sectional view of a display device according to an embodiment of the inventive concepts.

FIG. 7 is a cross-sectional view of a display device according to an embodiment.

As illustrated in FIG. 7, the display panel DP includes the base layer BL, and the circuit element layer DP-CL, light-emitting element layer DP-OLED, and thin-film encapsulation layer TFE, arranged on the base layer BL. The display panel DP may further include functional layers such as an anti-reflective layer, a refractive index adjustment layer, or the like.

The base layer BL may include a synthetic resin film. A synthetic resin layer is formed on a work substrate used when manufacturing the display panel DP. Thereafter, a conductive layer and an insulating layer are formed on the synthetic resin layer. When the work substrate is removed, the synthetic resin layer corresponds to the base layer BL. The synthetic resin layer may be a polyimide-based resin layer, but the material thereof is not particularly limited. In addition, the base layer BL may include a glass substrate, a metal substrate, an organic/inorganic composite material substrate, or the like.

The circuit element layer DP-CL includes at least one insulating layer and a circuit element. Hereinafter, the insulating layer included in the circuit element layer DP-CL will be referred to as an intermediate insulating layer. The intermediate insulating layer includes at least one intermediate inorganic film and at least one intermediate organic film. The circuit element includes a signal line, a pixel driving circuit, etc. The circuit element layer DP-CL may be formed through a process of forming an insulating layer, a semiconductor layer, and a conductive layer by coating, deposition, or the like and a process of patterning the insulating layer, the semiconductor layer, and the conductive layer by photolithography.

The light-emitting element layer DP-OLED may include a pixel defining film PDL and an organic light-emitting diode OLED. The pixel defining film PDL may include an organic material. A first electrode AE is arranged on the circuit element layer DP-CL. The pixel defining film PDL is formed on the first electrode AE. An opening OP is defined in the pixel defining film PDL. The opening OP of the pixel defining film PDL exposes at least a portion of the first electrode AE. In an alternative implementation of the embodiment, the pixel defining film PDL may not be provided.

A hole control layer HCL may be arranged on the first electrode AE. An emission layer EML is arranged on the hole control layer HCL. The emission layer EML may be arranged in a region corresponding to the opening OP. That is, the emission layer EML may be separately formed in each pixel PX (refer to FIG. 5). The emission layer EML may include an organic material and/or an inorganic material. The emission layer EML may generate predetermined color light.

An electron control layer ECL is disposed on the emission layer EML. A second electrode CE is disposed on the electron control layer ECL. The second electrode CE is commonly arranged in the pixel PX.

The thin-film encapsulation layer TFE is arranged on the second electrode CE. The thin-film encapsulation layer TFE seals the light-emitting element layer DP-OLED. The thin-film encapsulation layer TFE includes at least one insulating layer. The thin-film encapsulation layer TFE according to an embodiment may include at least one inorganic film (hereinafter referred to as an inorganic encapsulation film). The thin-film encapsulation layer TFE according to an embodiment may include at least one organic film (hereinafter referred to as an organic encapsulation film) and at least one inorganic encapsulation film.

The inorganic encapsulation film protects the light-emitting element layer DP-OLED from moisture/oxygen, and the organic encapsulation film protects the light-emitting element layer DP-OLED from foreign matter such as dust particles. The inorganic encapsulation film may include a silicon nitride layer, a silicon oxynitride layer, a silicon oxide layer, a titanium oxide layer, or an aluminum oxide layer, but is not particularly limited thereto. The organic encapsulation film may include an acryl-based organic film, but is not particularly limited.

The input sensor ISU includes a base layer IL1 and first and second conductive layers and first and second insulating layer IL2 and IL3 arranged on the base layer IL1. The base layer IL1 may include an inorganic material, for example, a silicon nitride layer. An inorganic film arranged on an uppermost side of the thin-film encapsulation layer TFE may also include a silicon nitride, wherein a silicon nitride layer of the thin-film encapsulation layer TFE and the base layer IL1 may be formed under different deposition conditions.

The first conductive layer is arranged on the base layer IL1. The first conductive layer may include the first sensing pattern SP1, the second sensing pattern SP2, and the second connection pattern CP2. The second conductive layer is arranged on the first conductive layer. The second conductive layer may include the first connection pattern CP1. The first insulating layer IL2 is arranged between the first conductive layer and the second conductive layer. The first insulating layer IL2 spaces and separates the first conductive layer and the second conductive layer in a cross-sectional view. A contact hole for partially exposing the first sensing pattern SP1 may be provided in the first insulating layer IL2, and the first connection pattern CP1 may be connected to the first sensing pattern SP1 via the contact hole. The second insulating layer IL3 is arranged on the first insulating layer IL2. The second insulating layer IL3 may cover the second conductive layer. The second insulating layer IL3 protects the second conductive layer from an external environment.

Mesh lines of the first sensing pattern SP1 and the second sensing pattern SP2 may define a plurality of mesh holes. The mesh lines may have a triple-layer structure of titanium/aluminum/titanium.

In a display device according to an embodiment, the input sensor ISU may be directly arranged on the display panel DP. The term "directly arrange" used herein represents that an additional adhesive film is not arranged between the input sensor ISU and the display panel DP. That is, the input sensor ISU may be formed on the display panel DP through a continuous process. In this case, the input sensor ISU may be referred to as an input sensing layer.

A portion in which the first electrode AE and the emission layer EML are arranged may be referred to as a pixel region PXA. The pixel regions PXA may be spaced apart from each other in the first direction DR1 and in the second direction DR2 (refer to FIG. 5). A non-pixel region NPXA may be arranged between the pixel regions PXA and may surround the pixel regions PXA.

The anti-reflective panel RPP may be arranged on an upper surface of the input sensor ISU. In an embodiment, the anti-reflective film panel RPP may include a polarizing film. The anti-reflective film panel RPP may further include a protective film and other functional films in addition to the polarizing film, but only the polarizing film is illustrated for convenience. The adhesive member AD1 may be arranged between the anti-reflective panel RPP and the input sensor ISU. Therefore, the anti-reflective panel RPP may be coupled to the input sensor ISU by the adhesive member AD1. The window WP may be coupled onto the anti-reflective panel RPP by the adhesive member AD2.

Referring back to FIG. 6, the input sensor ISU may be capacitive touch sensor. In an embodiment, any one of the first to 10th transmission electrodes TE1 to TE10 and the first to 14th reception electrodes RE1 to RE14 receives a transmission signal, and other one outputs, as a sensing signal, a change in capacity between the first to 10th transmission electrodes TE1 to TE10 and the first to 14th reception electrodes RE1 to RE14. In an embodiment, when the first transmission electrode TE1 receives a transmission signal (or driving signal), the first transmission electrode TE1 is capacitively coupled to the first to 14th reception electrodes RE1 to RE14. When a part of a user's body is positioned on a particular reception electrode among the capacitively coupled first to 14th reception electrodes RE1 to RE14, for example, the first reception electrode RE1, the capacity between the first transmission electrode TE1 and the first reception electrode RE1 changes. The readout circuit ROC (refer to FIG. 2) may calculate coordinate information about a touch position of the user by detecting a changed capacity of a sensing signal received from the first reception line RL1 connected to the first reception electrode RE1.

Figure 8:
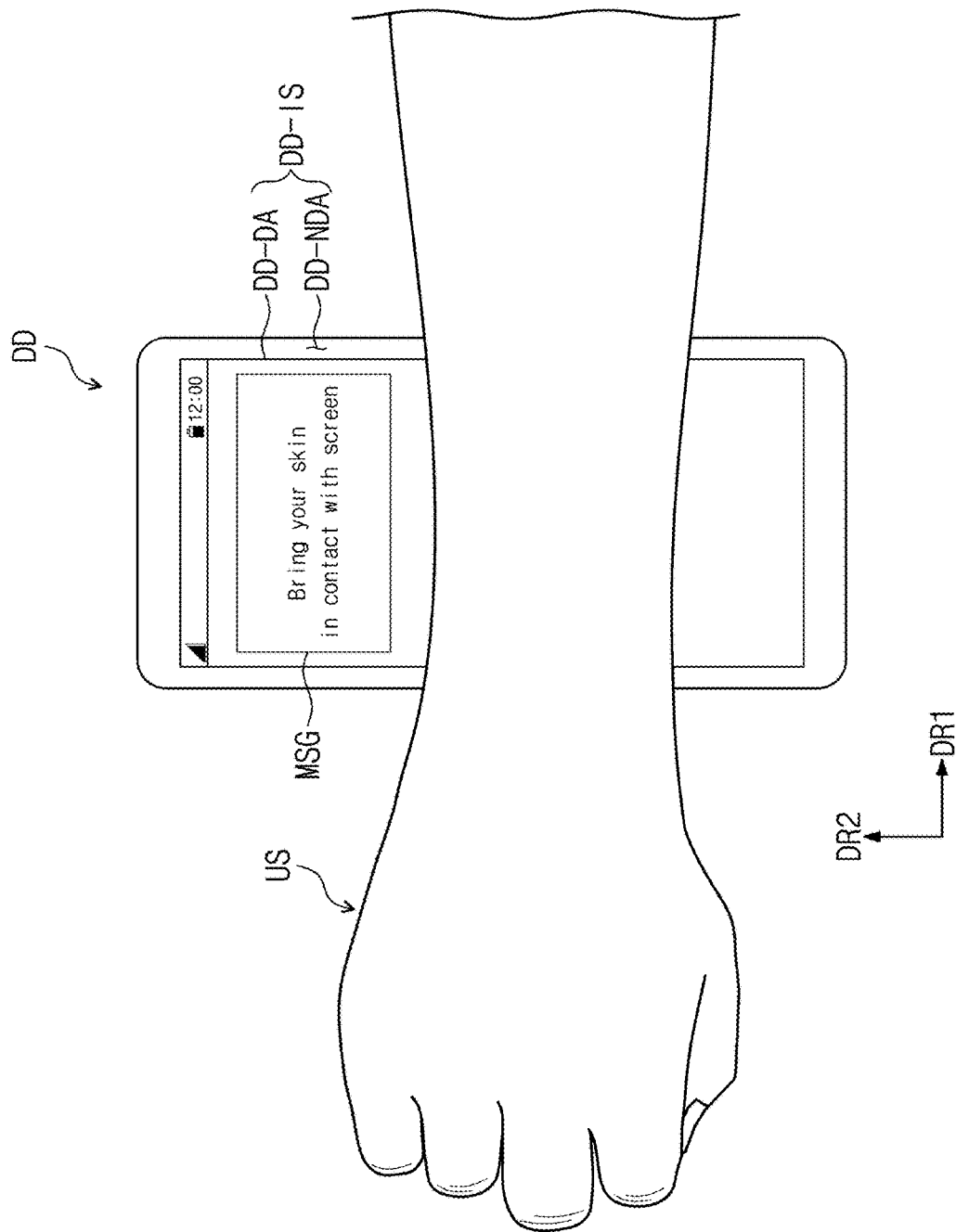
FIG. 8 is a diagram illustrating that a user measures a skin condition using a display device according to an embodiment of the inventive concepts.

FIG. 8 is a diagram illustrating that a user measures a skin condition using a display device according to an embodiment.

As illustrated in FIG. 8, the display device DD may display a message MSG indicating a beginning of a skin measurement mode in the image region DD-DA of the display surface DD-IS in the skin measurement mode. A user US confirms the message MSG while holding the display device DD with one hand, and brings the skin of a desired part of a user's US's body in contact with the image region DD-DA of the display device DD. In an embodiment, as illustrated in FIG. 8, the user US may bring the skin of an arm of the user US in contact with the image region DD-DA of the display device DD. Although FIG. 8 illustrates that a level of moisture of an inner wrist portion of the arm of the user US is measured, embodiments of the inventive concepts are not limited thereto. The user US may measure a body skin composition of various parts such as a face, a leg, an abdominal region, and the like.

The display device DD (refer to FIG. 1) may have a function of measuring and analyzing a body composition of a user US. The display device DD may use the input sensor ISU to obtain the body composition of the user US. A body composition measurement mode may be a mode in which the input sensor ISU operates to obtain information about the body composition of the user US. For example, the body composition may include muscle mass, body fat mass, moisture level, heart rate, blood pressure, skin elasticity, etc.

In an embodiment, when skin of a body comes in contact with the display surface DD-IS, capacity changes due to a permittivity difference between air and moisture in the skin. The display device DD may measure an amount of moisture in the skin by detecting such a variation in capacity.

For another example, a skin layer, a subcutaneous fat layer, and a muscle layer have different permittivities in a human body. The permittivity of a muscle layer may be lower than the permittivity of a subcutaneous fat layer. Therefore, as a thickness of a subcutaneous fat layer increases, the capacity between a transmission electrode and a reception electrode may increase. On the contrary, as the thickness of a subcutaneous fat layer reduces and a thickness of a muscle layer increases, the capacity between a transmission electrode and a reception electrode may decrease. Therefore, the input sensor ISU of the display device DD illustrated in FIG. 2 may measure the muscle mass and body fat mass of the user US.

As illustrated in FIGS. 6 and 8, when a wide area of the skin of the user US is in contact with the display surface DD-IS, two or more of the reception electrodes RE1 to RE14 may be capacitively coupled to one transmission electrode (e.g., TE1) simultaneously. In this case, it may be difficult to accurately measure the body composition. In particular, as a contact area between the skin of the user US and the display surface DD-IS increases, a noise component included in a reception signal may increase.

Figure 9:
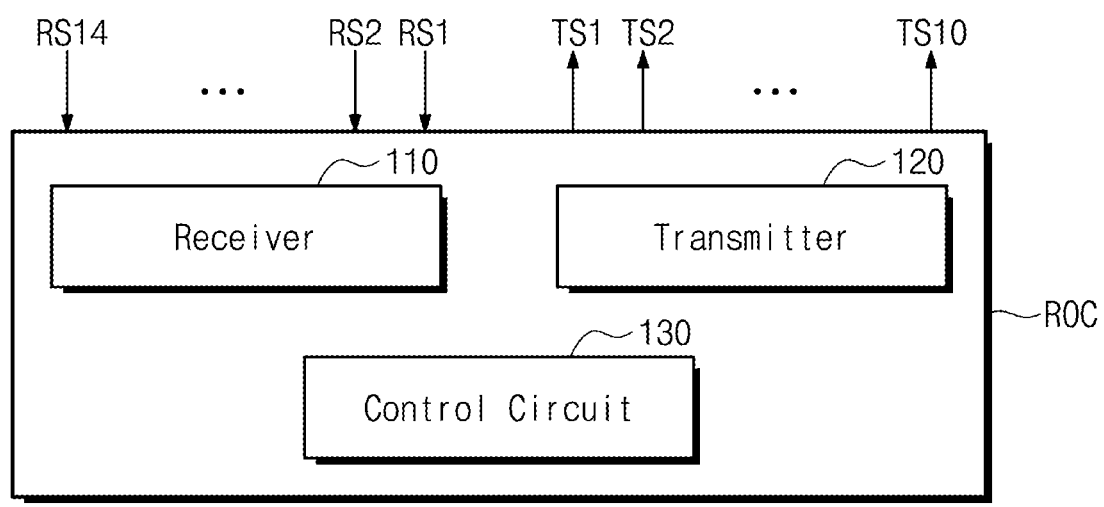
FIG. 9 illustrates signals transmitted or received to/from a readout circuit according to an embodiment of the inventive concepts.

FIG. 9 illustrates signals transmitted or received to/from a readout circuit according to an embodiment.

Referring to FIG. 9, the readout circuit ROC includes a receiver 110, a transmitter 120, and a control circuit 130.

The receiver 110 receives first to 14th reception signals RS1 to RS14 from the first to 14th reception electrodes RE1 to RE14. The first to 14th reception signals RS1 to RS14 received from the first to 14th reception electrodes RE1 to RE14 may be analog capacity signals generated due to the user input TC (refer to FIG. 1). The receiver 110 may include an analog front end (AFE) circuit for sensing an analog capacity signal.

In response to a control from the control circuit 130, the transmitter 120 transmits first to 10th transmission signals TS1 to TS10 to the first to 10th transmission electrodes TE1 to TE10.

The readout circuit ROC may control the first to 10th transmission signals TS1 to TS10 and the first to 14th reception signals RS1 to RS14 according to an operation mode. In a normal mode, the readout circuit ROC may provide the first to 10th transmission signals TS1 to TS10, which are in an active level, to all of the first to 10th transmission electrodes TE1 to TE10. Furthermore, in the normal mode, the readout circuit ROC receives all of the first to 14th reception signals RS1 to RS14 from the first to 14th reception electrodes RE1 to RE14.

In the body composition measurement mode, the readout circuit ROC may provide a portion of the first to 10th transmission signals TS1 to TS10 to corresponding electrodes among the first to 10th transmission electrodes TE1 to TE10. Furthermore, in the body composition measurement mode, the readout circuit ROC may receive a portion of the first to 14th reception signals RS1 to RS14 from a portion of the first to 14th reception electrodes RE1 to RE14.

Figure 10:
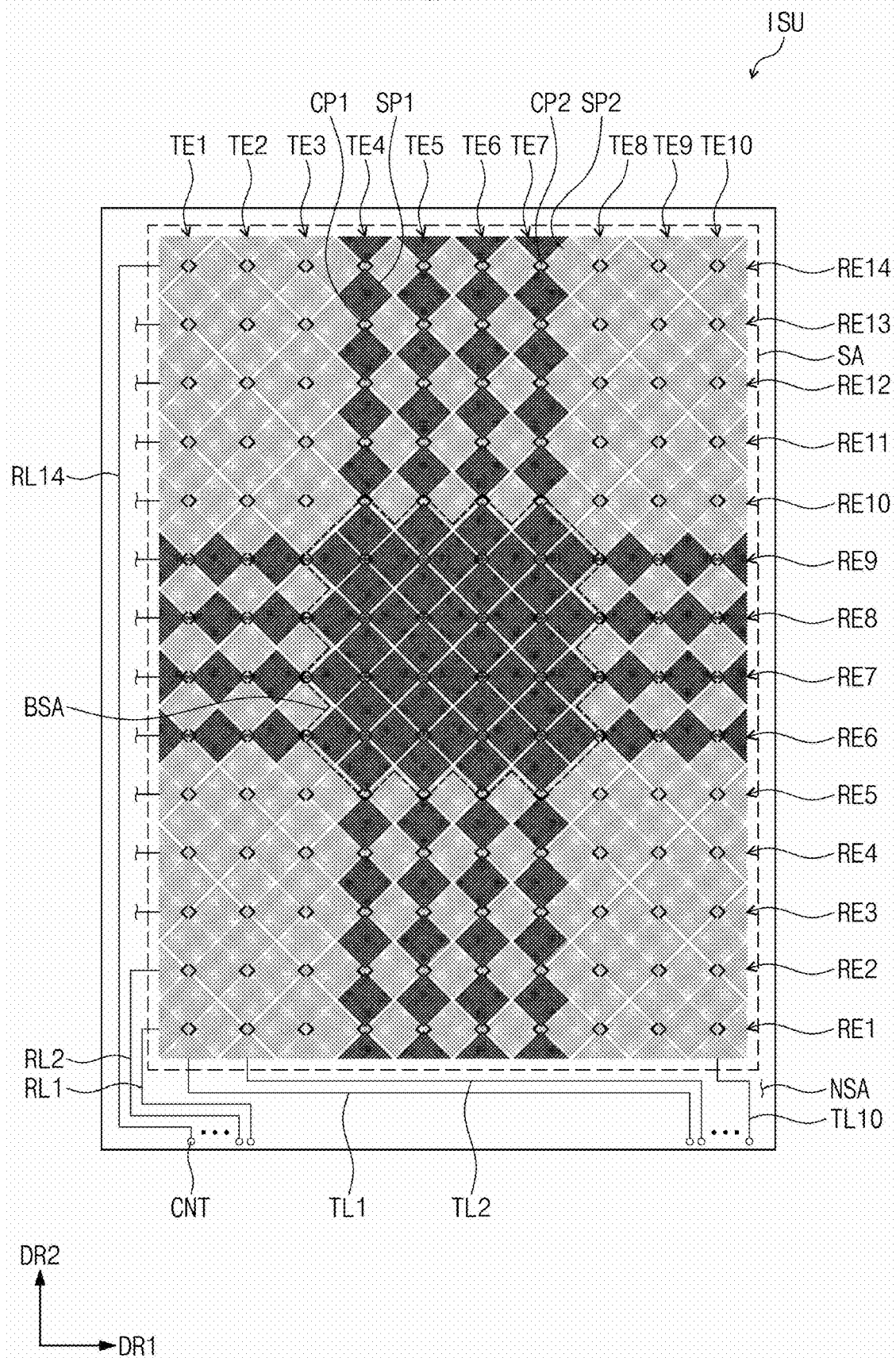
FIG. 10 is a diagram illustrating an example of an input sensor operating in the body composition measurement mode.

FIG. 10 is a diagram illustrating an example of the input sensor ISU operating in the body composition measurement mode.

Figure 11:
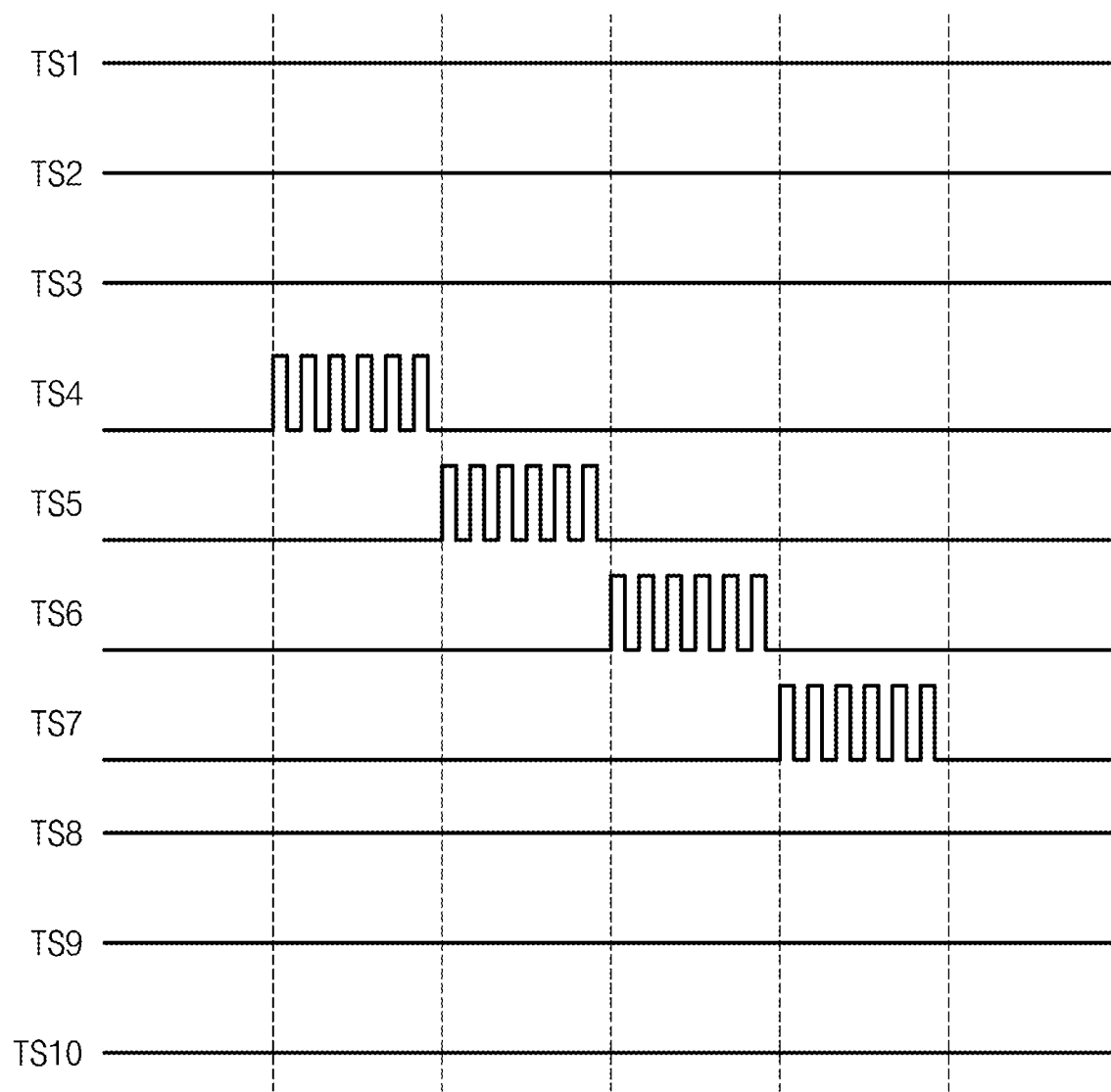
FIG. 11 is a timing diagram illustrating transmission signals provided to first to 10th transmission lines of the input sensor illustrated in FIG. 10.

FIG. 11 is a timing diagram illustrating the transmission signals TS1 to TS10 provided to the first to 10th transmission lines TL1 to TL10 of the input sensor ISU illustrated in FIG. 10.

Figure 12:
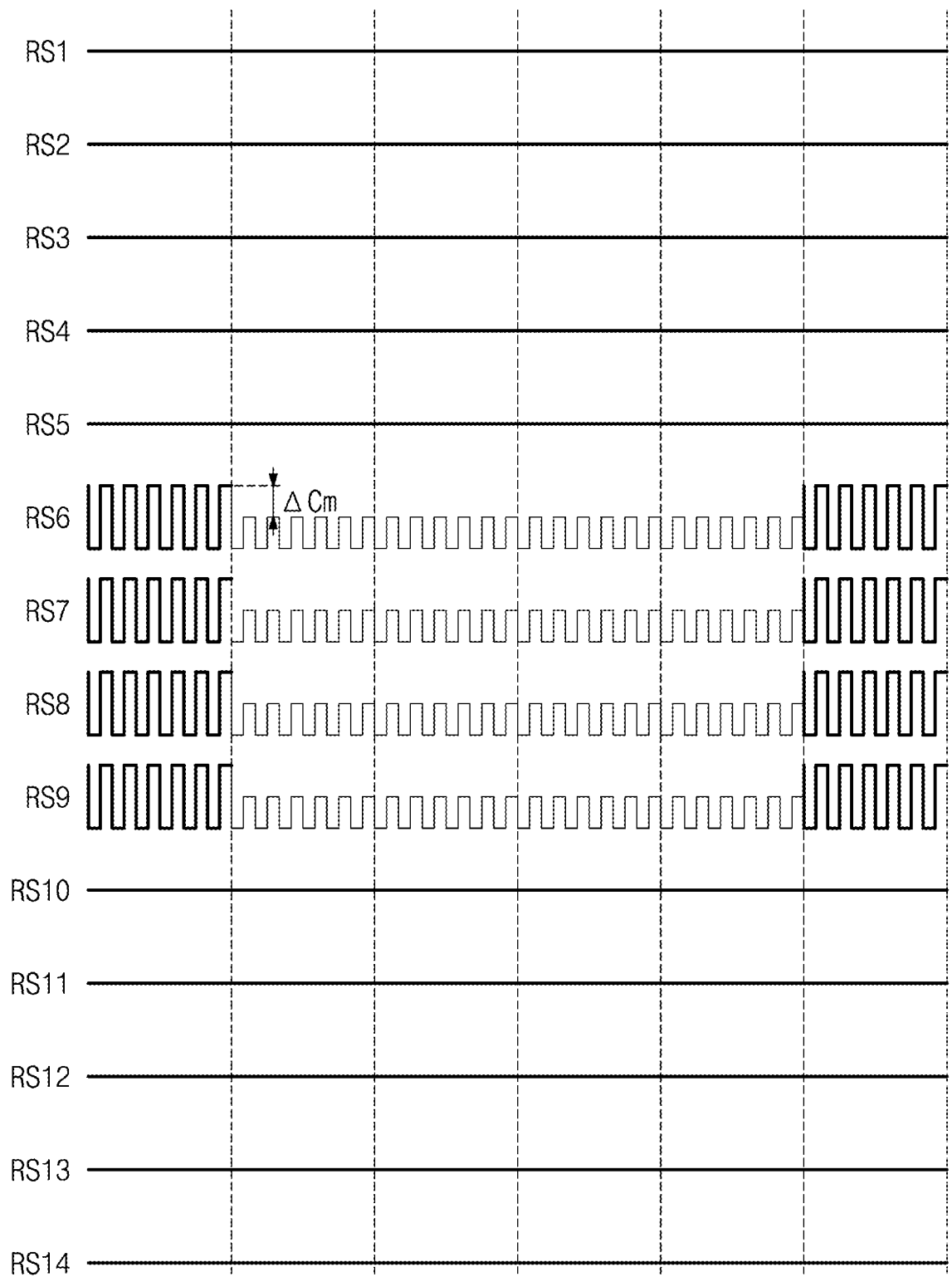
FIG. 12 is a timing diagram illustrating reception signals provided to first to 14th reception lines of the input sensor illustrated in FIG. 10.

FIG. 12 is a timing diagram illustrating the reception signals RS1 to RS14 provided to the first to 14th reception lines RL1 to RL14 of the input sensor ISU illustrated in FIG. 10.

Referring to FIGS. 9 to 12, in the body composition measurement mode, the input sensor ISU and the readout circuit ROC may sense an input to a partial region.

In the example illustrated in FIGS. 10 to 12, only a region in which the fourth to seventh transmission electrodes TE4 to TE7 and the sixth to ninth reception electrodes RE6 to RE9 intersect, i.e., a body composition sensing region BSA, may be subject to an input sensing operation. In the body composition measurement mode, the control circuit 130 sequentially outputs the transmission signals TS4 to TS7 to the fourth to seventh transmission electrodes TE4 to TE7 via the transmitter 120, and receives the reception signals RS6 to RS9 from the sixth to ninth reception electrodes RE6 to RE9 via the receiver 110. Here, the transmission signals TS1 to TS3 and TS8 to TS10 and the reception signals RS1 to RS5 and RS10 to RS14 may be in a floating state. That is, in the body composition measurement mode, the readout circuit ROC may maintain the transmission signals TS1 to TS3 and TS8 to TS10 and the reception signals RS1 to RS5 and RS10 to RS14 in a floating state. In an embodiment, in the body composition measurement mode, the readout circuit ROC may maintain the transmission signals TS1 to TS3 and TS8 to TS10 and the reception signals RS1 to RS5 and RS10 to RS14 at a ground voltage level.

When the fourth to seventh transmission signals TS4 to TS7, which are in an active level, are sequentially provided to the fourth to seventh transmission electrodes TE4 to TE7, a voltage (or current) of the sixth to ninth reception signals RS6 to RS9 may change according to a capacitance between the fourth to seventh transmission electrodes TE4 to TE7 and the sixth to ninth reception electrodes RE6 to RE9. The body composition of the user may be measured and analyzed based on a variation $\Delta Cm$ in the voltage (or current).

Although FIG. 10 illustrates that the body composition is sensed in the body composition sensing region BSA, in which the fourth to seventh transmission electrodes TE4 to TE7 among the first to 10th transmission electrodes TE1 to TE10 and the sixth to ninth reception electrodes RE6 to RE9 among the first to 14th reception electrodes RE1 to RE14 intersect, embodiments of the inventive concepts are not limited thereto. A size and location of the body composition sensing region BSA may be variously modified.

In an embodiment, the body composition sensing region BSA may correspond to at least one and less than 10 transmission electrodes among the first to 10th transmission electrodes TE1 to TE10 and at least one and less than 14 reception electrodes among the first to 14th reception electrodes RE1 to RE14.

Figure 13A:
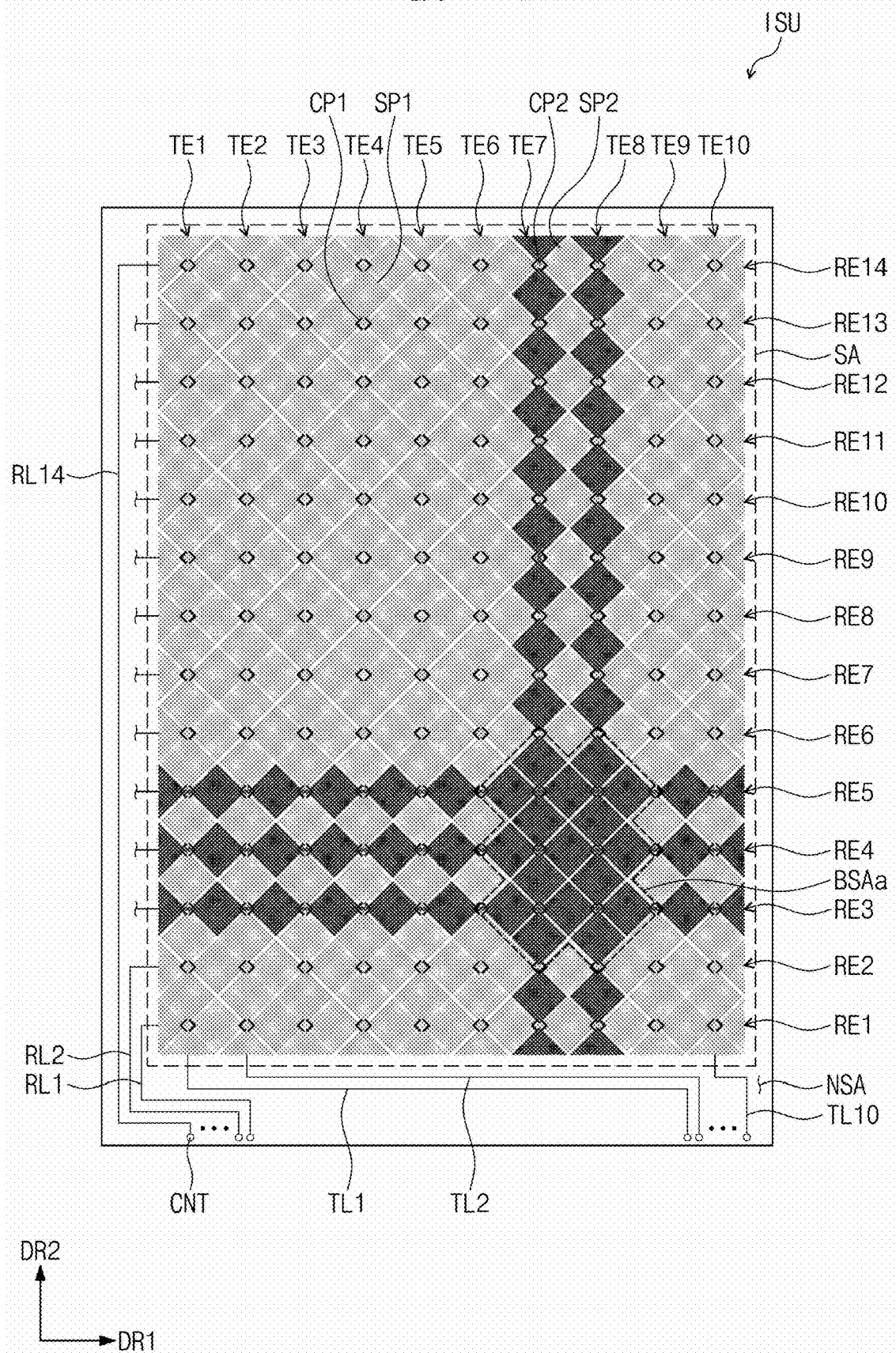
FIGS. 13A and 13B are diagrams illustrating body composition sensing regions of an input sensor.
Figure 13B:
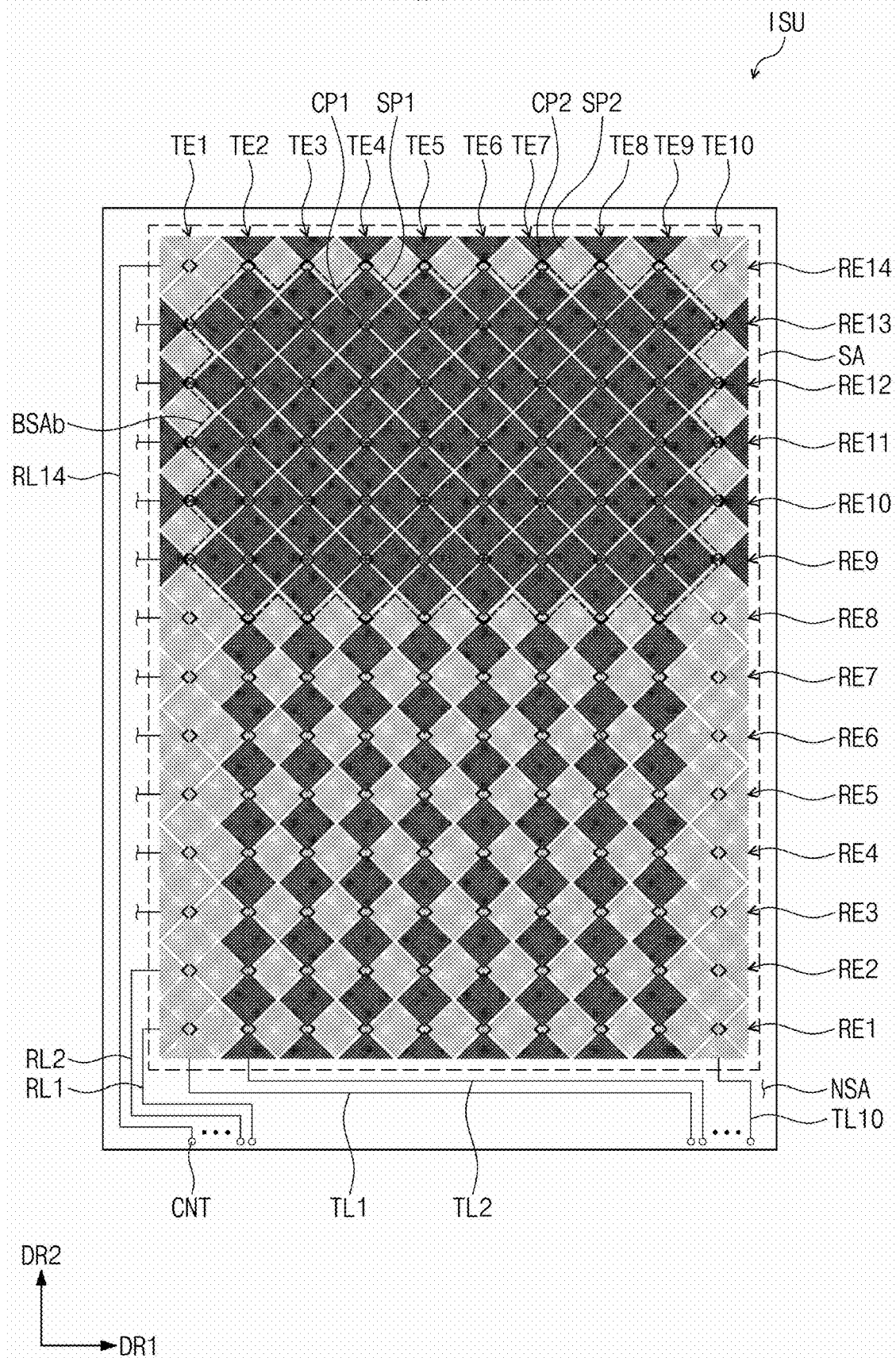

FIGS. 13A and 13B are diagrams illustrating body composition sensing regions of the input sensor ISU.

Referring to FIG. 13A, a body composition sensing region BSAa is a region in which the seventh and eighth transmission electrodes TE7 and TE8 and the third to fifth reception electrodes RE3 to RE5 intersect.

During the body composition sensing mode, the readout circuit ROC transmits the transmission signals TS7 and TS8, which are in an active level, to the seventh and eighth transmission electrodes TE7 and TE8. The readout circuit ROC may receive the third to fifth reception signals RS3 to RS5 from the third to fifth reception electrodes RE3 to RE5.

Referring to FIG. 13B, a body composition sensing region BSAb is a region in which the second to ninth transmission electrodes TE2 to TE9 and the ninth to 13th reception electrodes RE9 to RE13 intersect.

As illustrated in FIGS. 13A and 13B, sizes and locations of the body composition sensing regions BSAa and BSAb may be variously modified.

Figure 14A:
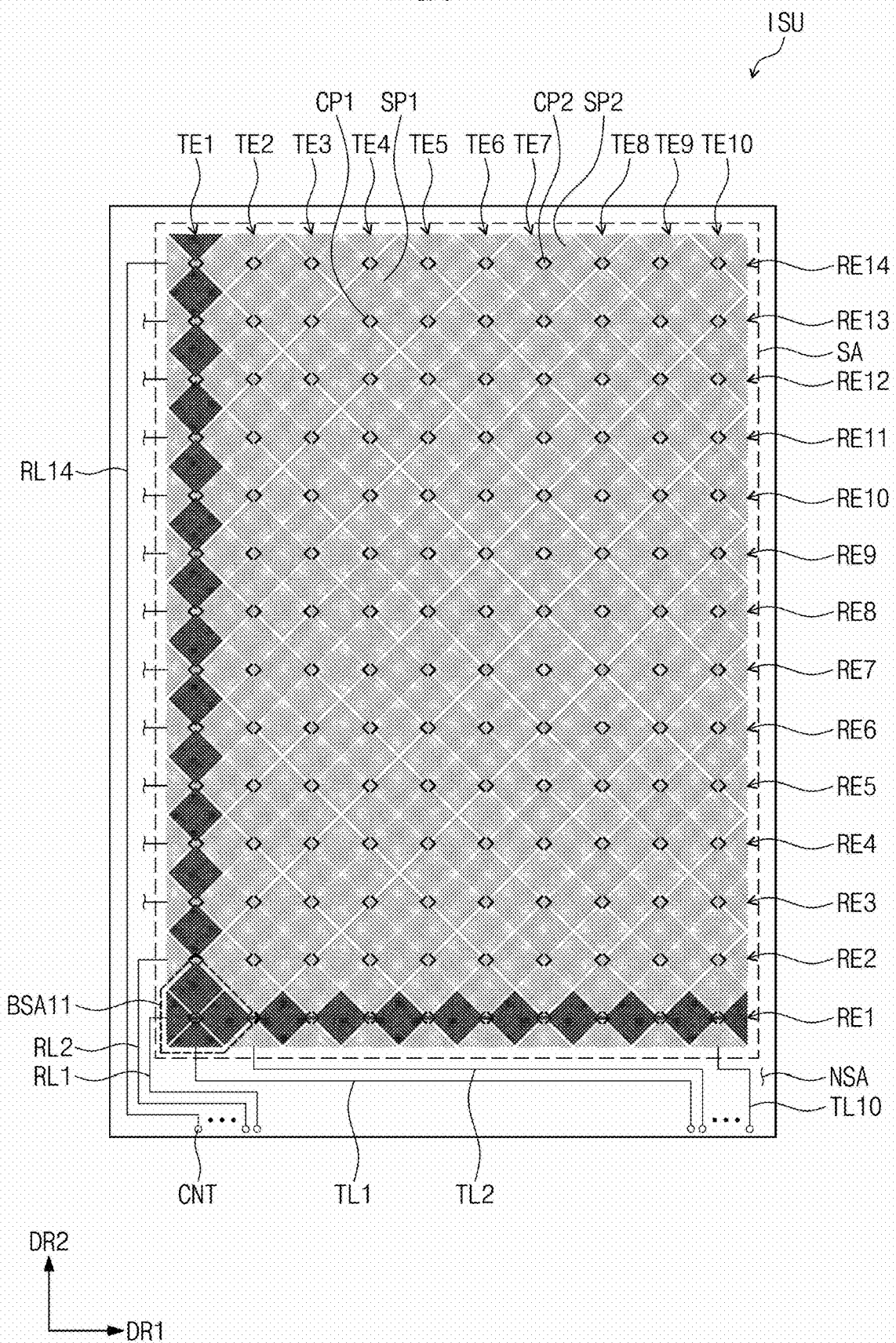
FIGS. 14A, 14B, and 14C are diagrams illustrating body composition sensing regions of an input sensor.
Figure 14B:
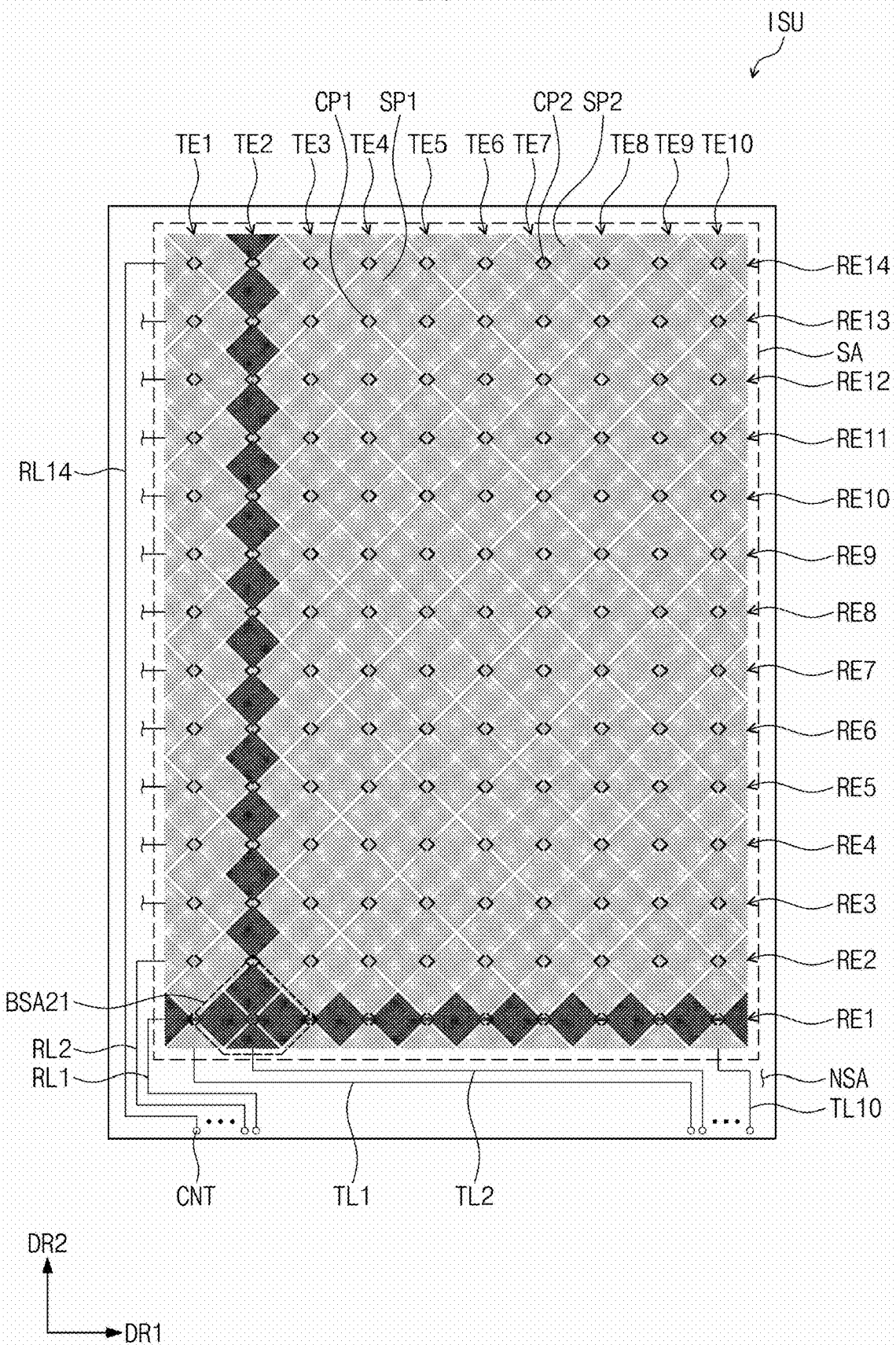
Figure 14C:
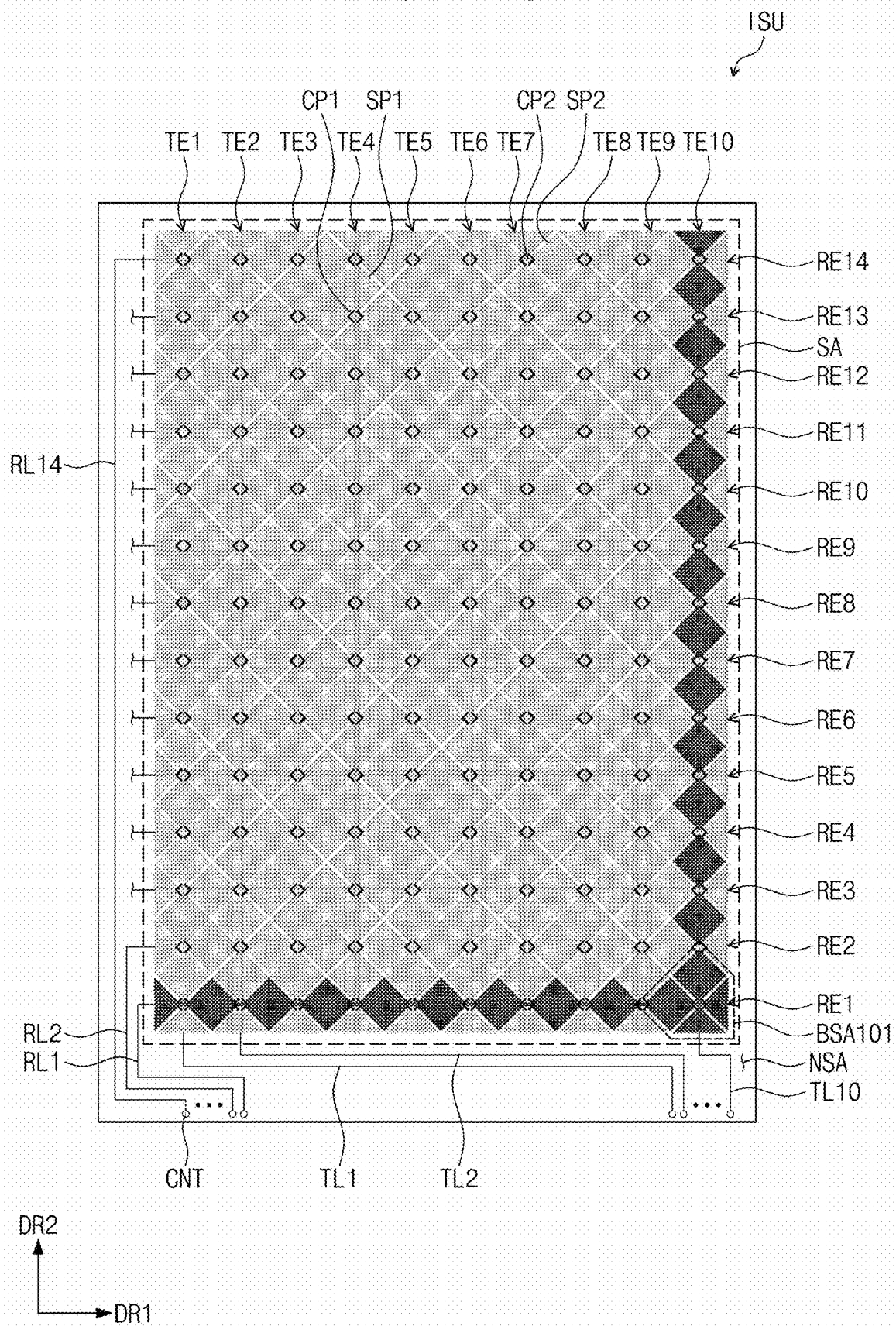

FIGS. 14A, 14B, and 14C are diagrams illustrating body composition sensing regions of the input sensor ISU.

Figure 15:
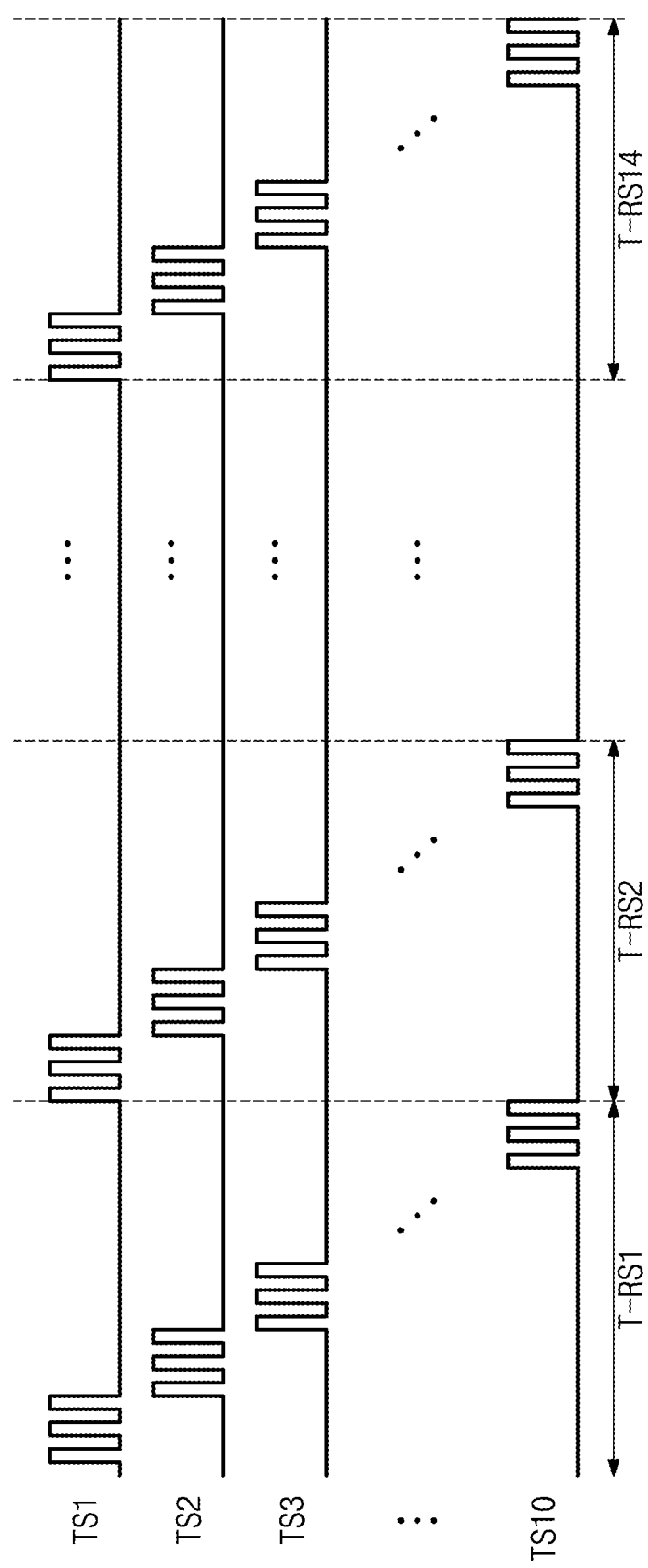
FIG. 15 is a timing diagram illustrating operation of an input sensor and a readout circuit.

FIG. 15 is a timing diagram illustrating operation of the input sensor ISU and the readout circuit ROC.

Referring to FIGS. 14A to 14C, the readout circuit ROC (refer to FIG. 9) sequentially drives the first to 10th transmission signals TS1 to TS10 one by one in an active level. While any one of the first to 10th transmission signals TS1 to TS10 is in an active level, the readout circuit ROC (refer to FIG. 9) sequentially receives the first to 14th reception signals RS1 to RS14 from the first to 14th reception electrodes RE1 to RE14.

In an embodiment, as illustrated in FIG. 14A, the readout circuit ROC provides the first transmission signal TS1, which is in an active level, to the first transmission electrode TE1, and receives the first reception signal RS1 from the first reception electrode RE1. Here, a body composition sensing region BSA11 is a region in which the first transmission electrode TE1 and the first reception electrode RE1 intersect.

As illustrated in FIG. 14B, the readout circuit ROC provides the second transmission signal TS2, which is in an active level, to the second transmission electrode TE2, and receives the first reception signal RS1 from the first reception electrode RE1. Here, a body composition sensing region BSA21 is a region in which the second transmission electrode TE2 and the first reception electrode RE1 intersect.

Furthermore, as illustrated in FIG. 14C, the readout circuit ROC provides the 10th transmission signal TS10 to the 10th transmission electrode TE10, and receives the first reception signal RS1 from the first reception electrode RE1. Here, a body composition sensing region BSA101 is a region in which the 10th transmission electrode TE10 and the first reception electrode RE1 intersect.

As illustrated in FIG. 15, the readout circuit ROC sequentially drives the first to 10th transmission signals TS1 to TS10 one by one in an active level during a first transmission/reception interval T-RS1, and receives the first reception signal RS1 from the first reception electrode RE1.

During a second transmission/reception interval T-RS2, the readout circuit ROC sequentially drives the first to 10th transmission signals TS1 to TS10 one by one in an active level, and receives the second reception signal RS2 from the second reception electrode RE2.

During a 14th transmission/reception interval T-RS14, the readout circuit ROC sequentially drives the first to 10th transmission signals TS1 to TS10 one by one in an active level, and receives the 14th reception signal RS14 from the 14th reception electrode RE14.

In this manner, the body composition of the user may be sensed in the entire sensing region SA of the input sensor ISU while sequentially changing the location of a body composition sensing region of the input sensor ISU.

Figure 16:
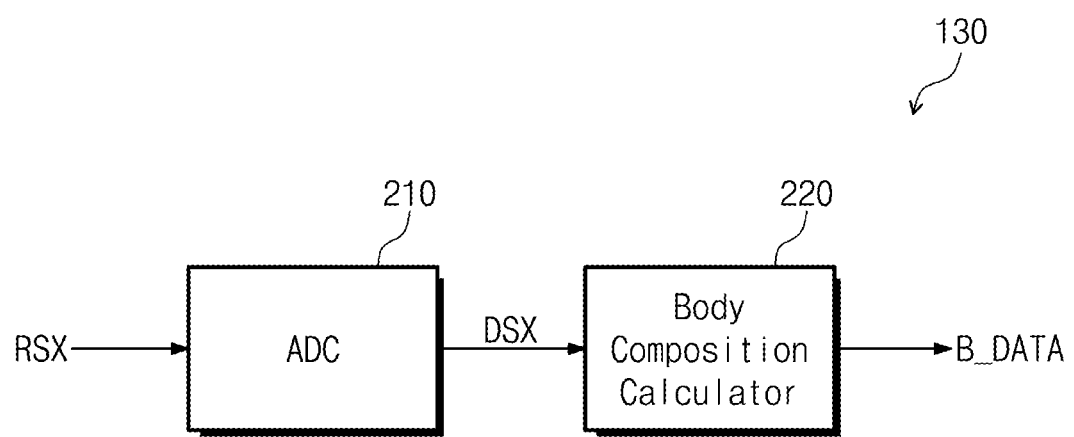
FIG. 16 is a block diagram illustrating a control circuit in a readout circuit.

FIG. 16 is a block diagram illustrating a control circuit in a readout circuit.

Referring to FIG. 16, the control circuit 130 includes an analog-to-digital converter 210 and a body composition calculator 220.

The analog-to-digital converter 210 converts a reception signal RSX received from the receiver 110 illustrated in FIG. 9 into a digital reception signal DSX.

The body composition calculator 220 calculates the body composition of the user US (refer to FIG. 8) based on the digital reception signal DSX. In an embodiment, when calculating a skin moisture level of the user US, the body composition calculator 220 may calculate a moisture level y through following Equation 1.

$$y = a + (b \times DSX) \quad (1)$$

In Equation 1, each of 'a' and 'b' may be a constant that is calculated through experimentation and statistics, i.e., set in advance.

The body composition calculator 220 outputs a body composition signal B_DATA corresponding to the calculated moisture level y.

Figure 17:
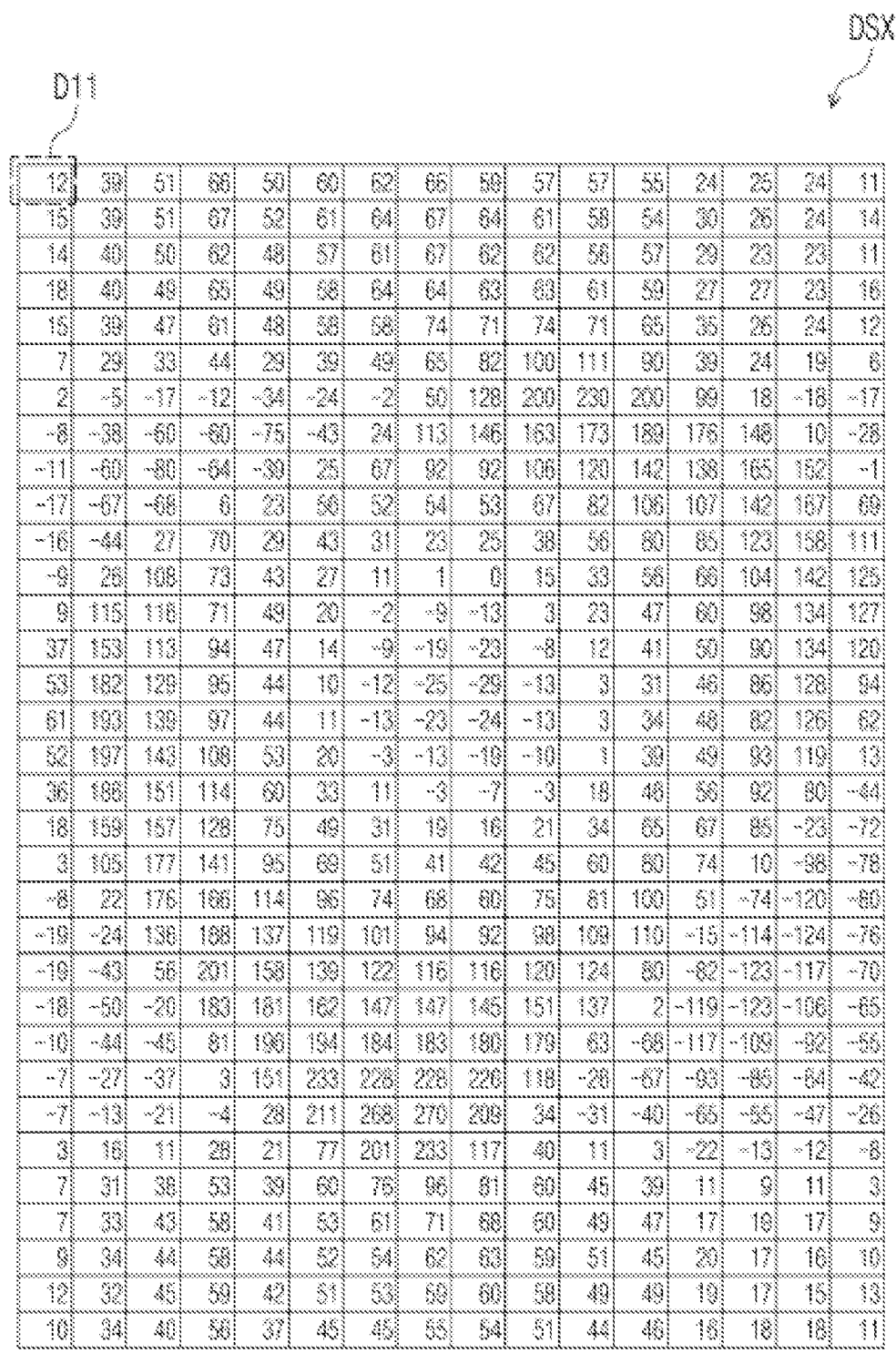
FIG. 17 is a diagram illustrating digital reception signals output from the analog-to-digital converter illustrated in FIG. 16.

FIG. 17 is a diagram illustrating the digital reception signal DSX output from the analog-to-digital converter 210 illustrated in FIG. 16.

In the case where the input sensor ISU illustrated in FIG. 6 includes 16 transmission electrodes arranged in the first direction DR1 and 33 reception electrodes arranged in the second direction DR2, the analog-to-digital converter 210 may output the digital reception signal DSX illustrated in FIG. 17.

In an embodiment, D11 included in the digital reception signal DSX illustrated in FIG. 17 may be a digital signal corresponding to the capacitance variation ΔCm between the first transmission electrode TE1 and the first reception electrode RE1 in the body composition sensing region BSA11 illustrated in FIG. 14A.

The analog-to-digital converter 210 illustrated in FIG. 16 outputs the digital reception signal DSX for the sensing region SA of the input sensor ISU (refer to FIG. 14A).

The digital reception signal DSX may be stored in a memory. The body composition calculator 220 may calculate a body composition with respect to the digital reception signal DSX according to an algorithm (e.g., Equation 1) stored in the memory.

In an embodiment, the body composition calculator 220 may calculate the skin moisture level of the user US (refer to FIG. 8) based on the digital reception signal DSX corresponding to a first region of the input sensor ISU (refer to FIG. 14A). The body composition calculator 220 may calculate the muscle mass of the user US (refer to FIG. 8) based on the digital reception signal DSX corresponding to a second region of the input sensor ISU (refer to FIG. 14A).

A display device having this configuration may measure a skin moisture level of a user and display a measurement result on a display panel. Therefore, user convenience of the use of a display device may be improved.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A display device comprising:
    a display panel configured to display an image;
    an input sensor arranged on the display panel and comprising a plurality of transmission electrodes and a plurality of reception electrodes electrically insulated from the plurality of transmission electrodes; and
    a readout circuit electrically connected to the input sensor,
    wherein the readout circuit is configured to sequentially output a transmission signal, which is in an active level, to the plurality of transmission electrodes, and to receive a reception signal from a first reception electrode among the plurality of reception electrodes during a first sensing period of a body composition sensing mode,
    wherein the readout circuit is configured to sequentially output a transmission signal, which is in an active level, to the plurality of transmission electrodes, and to receive a reception signal from a second reception electrode among the plurality of reception electrodes during a second sensing period of the body composition sensing mode, the second sensing period being different than the first sensing period,
    wherein the readout circuit comprises:

an analog-to-digital converter configured to convert the reception signal into a digital reception signal; and a body composition calculator configured to calculate a moisture level of a user based on the digital reception signal, wherein the body composition calculator calculates the moisture level y using a following equation $$y=a+(b \times DSX)$$

where each of 'a' and 'b' is a preset constant, and DSX denotes the digital reception signal.

2. The display device of claim 1, wherein the input sensor comprises:

a plurality of transmission lines respectively electrically connected to the plurality of transmission electrodes between the readout circuit and the plurality of transmission electrodes; and a plurality of reception lines respectively electrically connected to the plurality of reception electrodes between the readout circuit and the plurality of reception electrodes.

3. The display device of claim 2, wherein the readout circuit comprises:

a transmitter configured to output the transmission signal, which is in the active level, to the plurality of transmission lines;

a receiver configured to receive the reception signal from the plurality of reception lines; and a control circuit configured to control the transmitter and the receiver.

4. The display device of claim 1, wherein, during a normal mode, the readout circuit is configured to sequentially output the transmission signal, which is in an active level, to all of the plurality of transmission electrodes, and receive the reception signal from all of the plurality of reception electrodes.

5. The display device of claim 1, wherein each of the plurality of transmission electrodes and the plurality of reception electrodes has a mesh shape corresponding to mesh lines of a first sensing pattern and mesh lines of a second sensing pattern that together define a plurality of mesh holes.

6. The display device of claim 5, wherein the mesh lines of the first sensing pattern extend in a first direction that criss-crosses the mesh lines of the second sensing pattern that extend in a second direction that is orthogonal to the first direction.

* * * * *